United States Patent
Lee et al.

(10) Patent No.: US 12,257,330 B2
(45) Date of Patent: Mar. 25, 2025

(54) HAIR COLORING COMPOSITIONS AND METHODS OF USE

(71) Applicant: L'OREAL, Paris (FR)

(72) Inventors: Heather Lee, Wayne, NJ (US); Dongcui Li, Metuchen, NJ (US); Jun Liang, Staten Island, NY (US); Sarah Barrie Machover, New-York, NY (US); Sangeeta Gaikwad, Powai (IN)

(73) Assignee: L'OREAL, Paris (FR)

( * ) Notice: Subject to any disclaimer, the term of this patent is extended or adjusted under 35 U.S.C. 154(b) by 875 days.

(21) Appl. No.: 16/731,870

(22) Filed: Dec. 31, 2019

(65) Prior Publication Data

US 2020/0206112 A1 Jul. 2, 2020

Related U.S. Application Data

(60) Provisional application No. 62/786,887, filed on Dec. 31, 2018.

(51) Int. Cl.
| | |
|---|---|
| *A61K 8/34* | (2006.01) |
| *A61K 8/37* | (2006.01) |
| *A61K 8/41* | (2006.01) |
| *A61K 8/49* | (2006.01) |
| *A61K 8/73* | (2006.01) |
| *A61K 8/81* | (2006.01) |
| *A61Q 5/10* | (2006.01) |

(52) U.S. Cl.
CPC .............. *A61K 8/345* (2013.01); *A61K 8/342* (2013.01); *A61K 8/375* (2013.01); *A61K 8/416* (2013.01); *A61K 8/4946* (2013.01); *A61K 8/731* (2013.01); *A61K 8/8135* (2013.01); *A61K 8/8182* (2013.01); *A61Q 5/10* (2013.01); *A61K 2800/31* (2013.01); *A61K 2800/34* (2013.01); *A61K 2800/4324* (2013.01); *A61K 2800/48* (2013.01)

(58) Field of Classification Search
None
See application file for complete search history.

(56) References Cited

U.S. PATENT DOCUMENTS

| | | | | |
|---|---|---|---|---|
| 4,750,908 | A * | 6/1988 | Rosenbaum | ........... A61K 8/355 |
| | | | | 8/429 |
| 6,274,128 | B1 * | 8/2001 | Bergmann | ............... A61K 8/19 |
| | | | | 424/400 |
| 6,645,480 | B2 | 11/2003 | Giles | |
| 6,802,872 | B2 * | 10/2004 | Jo | ............. A61K 8/19 |
| | | | | 8/405 |
| 8,563,016 | B2 | 10/2013 | Agarelli et al. | |
| 2003/0103923 | A1 | 6/2003 | Ohta et al. | |
| 2006/0254000 | A1 | 11/2006 | Ducheron et al. | |
| 2007/0071703 | A1 | 3/2007 | Lin | |
| 2008/0107616 | A1 | 5/2008 | Hoffmann et al. | |
| 2008/0112912 | A1 * | 5/2008 | Springob | ............... A61K 8/891 |
| | | | | 424/70.12 |
| 2011/0135587 | A1 | 6/2011 | Kinoshita et al. | |
| 2011/0256083 | A1 | 10/2011 | Smith, Jr. et al. | |
| 2011/0268684 | A1 | 11/2011 | Battermann et al. | |
| 2013/0295033 | A1 * | 11/2013 | Yamazaki | ............... C08L 1/284 |
| | | | | 424/70.13 |
| 2014/0072523 | A1 | 3/2014 | Battermann et al. | |
| 2014/0196740 | A1 | 7/2014 | Mette et al. | |
| 2015/0150779 | A1 | 2/2015 | Delowsky et al. | |
| 2015/0174052 | A1 | 6/2015 | Mette et al. | |
| 2017/0216172 | A1 | 8/2017 | Carballada et al. | |
| 2018/0098923 | A1 | 4/2018 | Hutton, III | |

FOREIGN PATENT DOCUMENTS

| | | |
|---|---|---|
| EP | 2335671 A2 | 6/2011 |
| EP | 2335672 A2 | 6/2011 |
| EP | 2418002 A2 | 2/2012 |
| EP | 2594253 A2 | 5/2013 |
| GB | 2054664 A | 2/1981 |
| JP | 2016117715 A | 6/2016 |
| KR | 20080010846 A | 1/2008 |
| KR | 10-2012-0039384 A | 4/2012 |
| KR | 10-2013-0046109 A | 5/2013 |
| KR | 20130046109 A | 5/2013 |
| WO | 03037280 A1 | 5/2003 |
| WO | WO-2005/074875 A2 | 8/2005 |
| WO | 2009074463 A2 | 6/2009 |
| WO | 2009074464 A2 | 6/2009 |
| WO | 2009074465 A2 | 6/2009 |
| WO | 2010082487 A1 | 7/2010 |
| WO | 2011054612 A2 | 5/2011 |
| WO | WO-2012/156953 A2 | 11/2012 |
| WO | WO-2013/077072 A1 | 5/2013 |

OTHER PUBLICATIONS

International Search Report and Written Opinion issued on Apr. 1, 2020 for corresponding PCT Application No. PCT/US2019/069116.

* cited by examiner

*Primary Examiner* — H. Sarah Park

(74) *Attorney, Agent, or Firm* — POLSINELLI PC

(57) ABSTRACT

The present disclosure relates to hair coloring compositions; and to methods for coloring hair using the compositions. The hair coloring compositions are substantially anhydrous and include: one or more colorant; one or more glycols; one or more monoalcohols having from 2 to 6 carbon atoms; one or more cationic surfactants; and one or more fatty compounds.

3 Claims, No Drawings

HAIR COLORING COMPOSITIONS AND METHODS OF USE

FIELD OF THE DISCLOSURE

The present disclosure relates to hair coloring compositions; and to methods for coloring hair using the compositions.

BACKGROUND

There are many methods and products available for changing the natural color of hair. Semi-permanent or temporary dyeing methods, or direct dyeing methods, temporarily change the color of hair. These methods can change the color of the hair to varying degrees and the color change may withstand several rounds of shampooing. Many consumers seek more permanent results, and therefore default to oxidative dye products that contain hydrogen peroxide or other oxidants. In order to provide the consumer with the shade, longevity, and the intensity of color desired, an oxidative coloring process is utilized. Permanent hair dyeing formulations typically include primary intermediates (also known as oxidative hair dye precursors or developers) and couplers (also known as color modifiers or secondary intermediates). These dye precursors are sufficiently small, polar and soluble to diffuse into the hair shaft where, once activated by an oxidizing agent under basic conditions, such as hydrogen peroxide, the primary intermediates react with other dye precursors, e.g., couplers, to form larger colored chromophores in the hair shaft. The chromophores formed in the hair shaft do not readily diffuse from the hair during subsequent washing.

The oxidative coloring of hair can require long processing times. For instance, oxidative coloring processes involve premixing a coloring base and a developer. This mixture is then applied to the hair and must remain on the hair for a long period of time (an extended "processing" time) to potentiate the desired color change. Direct dyes, however, do not require admixing and activation by oxidizing agents and do not require long processing times.

Many attempts have been made by the hair color industry to enhance the washfastness (tenacity) of direct dyes by either forming a covalent bond between chromophore and proteins inside hair or increasing the number of binding sites, typically cationic centers, on the chromophore. However, each attempt has its drawbacks. The approach through covalent bonding does not differentiate proteins in hair from skin. The approach through multiple binding sites on the dyes (i.e. multiple positive charges to interact with negative sites on hair, either by bonding several monocationic dyes together or by installing multiple cationic centers on a single chromophore) runs into the obstacles of uneven color due to uneven damage (negative charges) along the length of the hair fibers and reduced dye penetration into hair fibers because the dyes are typically at least twice as large as common oxidative dye precursors. An increase in the number of binding sites minimizes bleeding and color loss caused by rinsing by providing stronger hair-chromophore interactions. However, the same strong binding force to the cuticle also prevents the chromophores from penetrating deep into the cortex of hair, because it is difficult for dyes with multiple positive charges to diffuse through negatively charged networks of keratin proteins. Additionally, since polycationic dyes remain bound to the hair surface rather than penetrating into the fiber, it is difficult to produce dark shades, due to limited binding sites on the surface of hair.

SUMMARY OF THE DISCLOSURE

The instant disclosure relates to hair coloring compositions; and to methods for coloring the hair using the compositions. Upon application to wet or damp hair, the compositions form a lamellar phase, which surprisingly enhances the deposition of colorants (e.g., direct dyes and oxidative dyes) and conditioning active agents (such as cationic surfactants and fatty compounds) onto the hair. The enhanced deposition of colorants improves the coloring of hair while the enhanced deposition of conditioning active agents provides a smoothing and softening effect to the hair. The result is vibrantly colored hair having a shiny and nourished appearance. The coloring compositions typically include:
  one or more colorant comprising at least one of an oxidative dye precursor, a coupler, a direct dye, or a combination thereof;
  one or more glycols;
  one or more monoalcohols having from 2 to 6 carbon atoms;
    wherein the weight ratio of the glycol(s) to the monoalcohol(s) (glycols:monoalcohol(s)) is from 20:1 to 1:1;
  one or more cationic surfactants;
  one or more non fatty compounds;
  wherein the composition is a solubilized, non-emulsified composition until applied to the wet or damp hair, whereupon the composition forms a lamellar phase in situ. The compositions are typically applied to wet or damp hair, and massaged into the hair to ensure uniform coverage. After application to the hair, the hair may be rinsed with water, dried, and styled as desired.

DETAILED DESCRIPTION OF THE DISCLOSURE

The present disclosure relates to a coloring composition that is substantially anhydrous comprising:
  one or more colorant comprising at least one of an oxidative dye precursor, a coupler, a direct dye, or a combination thereof;
  about 20 to about 90 wt. % of one or more glycols;
  about 5 to about 70 wt. % of one or more monoalcohols having from 2 to 6 carbon atoms;
  wherein the weight ratio of the glycol(s) to the monoalcohol(s) (glycols:monoalcohol(s)) is from 20:1 to 1:1;
  about 0.1 to about 10 wt. % of one or more cationic surfactants; and
  about 1 to about 20 wt. % of one or more fatty compounds;
  wherein the composition is a solubilized, non-emulsified composition until applied to the wet or damp hair, whereupon the composition forms a lamellar phase in situ; and all percentages by weight are based on the total weight of the composition.

Preferably, the compositions are essentially anhydrous. The phrase "essentially anhydrous" is interchangeable with the phrase "essentially free of water" or "substantially free of water." An essentially anhydrous composition may include no water or may include insignificant amounts of water, for example, less than 5 wt. % of water, based on the total weight of the composition. Nonetheless, the essentially anhydrous composition may include less than 4 wt. %, less than 3 wt. %, less than 2 wt. %, less than 1 wt. %, or less than 0.5 wt. % of water.

The compositions of the instant disclosure typically have a viscosity of about 10 mPa·s to about 10,000 mPa·s at 25° C. The viscosity measurements can be carried out, for example, using a Brooksfield viscometer, Model RVT (Brookfield Engineering Laboratories, Inc.) at about 20 revolutions per minute (RPM), at ambient room temperature of about 20 to 25° C.; spindle sizes may be selected in accordance with the standard operating recommendations form the manufacturer, ranging from disk spindle No. 1 to No. 4.

Direct dyes, also called substantive dyes, are a class of colored compounds that are typically water-soluble and have an affinity for fibers such as hair. Direct dyes can be applied to fibers, such as hair, without the use of a mordent and are often azo and nitro compounds. In some instances, the only hair coloring compounds in the hair-coloring compositions are direct dyes, for example, direct dyes selected from nitro-phenylenediamines, nitro-aminophenols, azo dyes, anthraquinones, triarylmethane dyes, indophenols, and a mixture thereof. A more exhaustive but non-limiting list of useful direct dyes is included under the heading, "Direct Dyes."

The total amount of colorants (e.g., direct dyes, oxidative dye precursors, couplers) in the compositions may vary but is typically from about 0.001 to about 10 wt. %, based on the total weight of the composition. In some cases, the total amount of colorants may be from about 0.001 to about 8 wt. %, about 0.001 to about 6 wt. %, about 0.001 to about 5 wt. %, about 0.001 to about 4 wt. %, about 0.001 to about 3 wt. %, about 0.01 to about 10 wt. %, about 0.01 to about 8 wt. %, about 0.01 to about 6 wt. %, about 0.01 to about 5 wt. %, about 0.01 to about 4 wt. %, about 0.01 to about 3 wt. %, about 0.1 to about 10 wt. %, about 0.1 to about 8 wt. %, about 0.1 to about 6 wt. %, or about 0.1 to about 5 wt. %, about 0.1 to about 4 wt. %, or about 0.1 to about 3 wt. %, based on the total weight of the composition.

The compositions may, optionally, be non-oxidative compositions that are therefore free or essentially free of oxidative dye precursors. "Non-oxidative" means that the hair coloring composition does not require oxidizing agents (such as, for example, hydrogen peroxide) to chemically change the color of the hair. A hair-coloring composition that is "free of oxidizing agents that alter the color of hair" may include substances that have the ability to oxidize other substances, but the coloring compositions do not rely on this mode of action to achieve the desired coloring of the hair.

The compositions include one or more glycols. Non-limiting examples of glycols include ethylene glycol, propylene glycol, butylene glycol, hexylene glycol, pentylene glycol, diethylene glycol, dipropylene glycol, 1,3 propanediol, and glycerin. The total amount of glycol(s) can vary but is typically about 20 to about 90 wt. %, based on the total weight of the composition. Propylene glycol is particularly preferred. In some instances, the total amount of glycol(s) is about 30 to about 90 wt. %, about 40 to about 90 wt. %, or about 50 to about 90 wt. %, Similarly, is some cases, the total amount of glycol(s) may be about 20 to about 80 wt. %, about 30 to about 80 wt. %, about 40 to about 80 wt. %, or about 50 to about 80 wt. %, including ranges and sub-ranges therebetween, based on the total weight of the composition.

The compositions include one or more monoalcohols having from 2 to 6 carbon atoms. For example, the one or more monoalcohols may be selected from ethanol, propanol, butanol, pentanol, hexanol, isopropyl alcohol, cycohexanol, isobutyl alcohol, 2-methyl-2-butanol (2-methylbutan-2-ol), and a mixture thereof.

The total amount of monoalcohols can vary but is typically from about 5 to about 70 wt. %, based on the total weight of the composition. In some instances, the total amount of monoalcohols is from about 5 to about 60 wt. %, about 5 to about 50 wt. %, about 5 to about 45 wt. %, about 5 to 40 wt. %, about 5 to 35 wt. %, about 5 to about 30 wt. %, about 10 to about 70 wt. %, about 10 to about 60 wt. %, about 10 to about 50 wt. %, about 10 to about 45 wt. %, about 10 to about 40 wt. %, about 10 to about 35 wt. %, or about 10 to about 30 wt. %, including ranges and sub-ranges therebetween based on the total weight of the composition.

In some instances, the one or more monoalcohols include ethanol. For example, the compositions may include ethanol and optionally one or more additional monoalcohols having from 2 to 6 carbon atoms. The total amount of ethanol may vary but it typically from about 5 to about 60 wt. %, based on the total weight of the composition. In some instances, the total amount of ethanol is from about 5 to about 50 wt. %, about 5 to about 45 wt. %, about 5 to about 40 wt. %, about 5 to 35 wt. %, about 5 to about 30 wt. %, about 10 to about 70 wt. %, about 10 to about 60 wt. %, about 10 to about 50 wt. %, about 10 to about 45 wt. %, about 10 to about 40 wt. %, about 10 to about 35 wt. %, or about 10 to about 30 wt. %, including ranges and sub-ranges therebetween, based on the total weight of the composition.

The total amount of glycol(s) is typically at least the same or higher than the total amount of the monoalcohol(s) having from 2 to 6 carbon atoms in the compositions. Often, the compositions include more glycol(s) than monoalcohol(s) having from 2 to 6 carbon atoms, i.e., a higher weight percent of the composition is glycol(s) than monoalcohols having from 2 to 6 carbon atoms. The ratio of glycol(s) to the total amount of monoalcohol(s) having from 2 to 6 carbon atoms (glycol (s):monoalcohol(s)) may be from 20:1 to 1:1. In some instances, the ratio is from 20:1 to 1.1:1, 20:1 to 1.5:1, or 20:1 to 2:1, including ranges and sub-ranges therebetween. Similarly, in some instances, the ratio is from 18:1 to 1:1, 18:1 to 1.1:1, 18:1 to 1.5 to 1, 18:1 to 2:1, including ranges and sub-ranges therebetween.

The term "cationic surfactant" means a surfactant that may be positively charged when it is contained in the compositions according to the disclosure. This surfactant may bear one or more positive permanent charges or may contain one or more functional groups that are cationizable in the composition according to the disclosure. Non-limiting examples of cationic surfactants include cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, brassicamidopropyldimethylamine, lauramidopropyl dimethylamine, myristamidopropyl dimethylamine, dilinoleamidopropyl dimethylamine, palmitamidopropyl dimethylamine, and mixtures thereof.

In some instances, the cationic surfactant is preferably selected from cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethylamine, behenamidoethyldimethylamine, arachidamidopropyldimethylamine, arachidamido-propyidiethylamine, arachidamidoethyidiethylamine, arachidamidoethyidimethylamine, and mixtures thereof.

In some instances, the cationic surfactants are more preferably selected from cetrimonium chloride, behentrimonium chloride, behentrimonium methosulfate, stearamidopropyl dimethylamine, and a mixture thereof.

Moreover, in some cases, the cationic surfactant is most preferably cetrimonium chloride, behentrimonium chloride, or a mixture thereof.

A more exhaustive list of cationic surfactants that may be included in the hair-treatment compositions is provided later, under the heading "Cationic Surfactants."

The total amount of cationic surfactant(s) in the composition can vary but is typically from about 0.1 to about 10 wt. %, based on the total weight of the composition. In some cases, the total amount of cationic surfactant(s) is from about 0.1 to about 8 wt. %, about 0.1 to about 5 wt. %, about 0.1 to about 3 wt. %, about 0.1 to about 2 wt. %, about 0.5 to about 10 wt. %, about 0.5 to about 8 wt. %, about 0.5 to about 5 wt. %, about 0.5 to about 3 wt. %, or about 0.5 to about 2 wt. %, including ranges and sub-ranges therebetween, based on the total weight of the composition.

Non-limiting examples of fatty compounds include fatty esters, fatty alcohols, glyceryl esters (glycerol esters), fatty acids, fatty esters, alkyl ethers of fatty alcohols, fatty acid esters of fatty alcohols, fatty acid esters of alkyl ethers of fatty alcohols, fatty acid esters of alkoxylated fatty alcohols, fatty acid esters of alkyl ethers of alkoxylated fatty alcohols, hydroxy-substituted fatty acids, and mixtures thereof. Non-limiting examples of fatty esters include fatty carbonate esters, glycerol fatty esters, sucrose fatty esters, sorbitan fatty ester, fatty acid esters, or mixtures thereof. Non-limiting examples of the fatty alcohols, fatty acids, fatty alcohol derivatives, and fatty acid derivatives are found in International Cosmetic Ingredient Dictionary, Sixteenth Edition, 2016, which are incorporated by reference herein in its entirety. A more exhaustive but non-limiting list of useful fatty compounds is provided later, under the heading "fatty compounds."

The total amount of fatty compounds in the compositions may vary but is typically from about 0.1 to about 20 wt. %, based on the total weight of the composition. The total amount of fatty compounds may be from about 0.1 to about 15 wt. %, about 0.1 to about 10 wt. %, about 0.1 to about 8 wt. %, about 0.1 to about 5 wt. %, about 0.5 to about 20 wt. %, about 0.5 to about 15 wt. %, about 0.5 to about 10 wt. %, about 0.5 to about 8 wt. %, about 0.5 to 5 wt. %, about 1 to about 20 wt. %, about to about 15 wt. %, about 1 to about 10 wt. %, about 1 to about 8 wt. %, or about 1 to about 5 wt. %, including ranges and sub-ranges therebetween, based on the total weight of the composition.

In some instances, the compositions of the instant disclosure include one or more fatty esters, i.e., one or more of the fatty compound(s) is a fatty ester. Non-limiting examples of fatty esters include fatty carbonate esters (in particular dialkyl carbonates), glycerol fatty esters, sucrose fatty esters, sorbitan fatty ester, fatty acid esters, or mixtures thereof. Additional non-limiting examples of fatty esters that may be used include fatty esters such as esters of $C_{6-22}$ fatty acids with a monohydric alcohol and/or esters of $C_{6-22}$ fatty alcohols with a monocarboxylic acid. More specific non-limiting examples include isopropyl isostearate, n-propyl myristate, isopropyl myristate, hexyl laurate, hexadecyl isostearate, hexyldecyl laurate, hexyldecyl octanoate, n-propyl palmitate, isopropyl palmitate, and mixtures thereof.

Preferable fatty esters include fatty carbonate esters (also referred to as "fatty carbonates"). Fatty carbonates include dialkyl carbonates. Non-limiting examples of dialkyl carbonates include those of the following formula: $R_1O(C=O)R_2$, wherein $R_1$ and $R_2$ are independently linear or branched, saturated or unsaturated alkyl chains having 1 to 30 carbon atoms, or having 2 to 28 carbon atoms, or having 4 to 25 carbon atoms, or having 6 to 22 carbon atoms, for example, C14-15 dialkyl carbonate, dicaprylyl carbonate, diethyl carbonate, dihexyl carbonate, diethylhexyl carbonate, dimethoxyphenyl phenyloxyethyl ethylcarbonate, dimethyl carbonate, dipropyl carbonate, dipropylheptyl carbonate, dioctyl carbonate, and a mixture thereof. In some instances, it is preferable to include one or more dialkyl carbonates, in particular dicaprylyl carbonate.

In some cases, the one or more fatty esters is a glycerol ester of fatty acids or glyceryl esters (or glycerol fatty esters), for example, glyceryl monomyristate, glyceryl monopalmitate, glyceryl monostearate, glyceryl isostearate, glyceryl monooleate, glyceryl dioleate, glyceryl distearate, glyceryl laurate, trilaurin, triarachidin, tribehenin, tricaprin, tricaprylin, caprylic/capric triglyceride, trierucin, triheptanoin, triheptylundecanoin, triisononanoin, triisopalmitin, triisostearin, trilinolein, trimyristin, trioctanoin, triolein, tripalmitin, tripalmitolein, triricinolein, tristearin, triundecanoin, and mixtures thereof.

Additional, non-limiting examples of fatty esters include diisobutyl adipate, 2-hexyldecyl adipate, di-2-heptylundecyl adipate, monoisostearic acid N-alkyl glycol, isocetyl isostearate, trimethylolpropane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, neopentyl glycol dicaprate, triethyl citrate, 2-ethylhexyl succinate, isocetyl stearate, butyl stearate, diisopropyl sebacate, di-2-ethylhexyl sebacate, cetyl lactate, myristyl lactate, isopropyl palm itate, 2-ethylhexyl palm itate, 2-hexyldecyl palm itate, 2-heptylundecyl palm itate, cholesteryl 12-hydroxystearate, dipentaerythritol fatty acid ester, isopropyl myristate, octyldodecyl myristate, 2-hexyldecyl myristate, myristyl myristate, hexyldecyl di methyloctanoate, ethyl laurate, hexyl laurate, diisostearyl malate, dicaprylyl carbonate, and mixtures thereof.

The total amount of the fatty ester(s) in the composition, if present, may vary but is typically from about 0.1 to about 15 wt. %, based on the total weight of the composition. In some instances, the total amount of fatty ester(s) is from about 0.1 to about 12 wt. %, about 0.1 to about 10 wt. %, about 0.1 to about 8 wt. %, about 0.1 to about 5 wt. %, about 0.5 to about 15 wt. %, about 0.5 to about 12 wt. %, about 0.5 to about 10 wt. %, about 0.5 to about 8 wt. %, or about 0.5 to about 5 wt. %, based on the total weight of the composition.

In some instances, the compositions of the instant disclosure include one or more fatty alcohols, i.e., one or more of the fatty compound(s) is a fatty alcohol. The term "fatty alcohol" means an alcohol comprising at least one hydroxyl group (OH), and comprising at least 8 carbon atoms, and which is neither oxyalkylenated (in particular neither oxyethylenated nor oxypropylenated) nor glycerolated. The fatty alcohols can be represented by: R—OH, wherein R denotes a saturated (alkyl) or unsaturated (alkenyl) group, linear or branched, optionally substituted with one or more hydroxyl groups, comprising from 8 to 40 carbon atoms, preferably 10 to 30 carbon atoms, more preferably 12 to 24 carbon atoms, and even more preferably 14 to 22 carbon atoms.

In some instances, the compositions include at least one solid fatty alcohol. It is preferable that the solid fatty alcohols are solid at ambient temperature and at atmospheric pressure (25° C., 780 mmHg), and are insoluble in water, that is to say they have a water solubility of less than 1% by weight, preferably less than 0.5% by weight, at 25° C., 1 atm.

The solid fatty alcohols may be represented by: R—OH, wherein R denotes a linear alkyl group, optionally substituted with one or more hydroxyl groups, comprising from 8 to 40 carbon atoms, preferably 10 to 30 carbon atoms, more preferably 12 to 24 carbon atoms, and even more preferably 14 to 22 carbon atoms.

In particular, it is possible to mention, alone or as a mixture: lauryl alcohol or lauryl alcohol (1-dodecanol); myristic or myristyl alcohol (1-tetradecanol); cetyl alcohol (1-hexadecanol); stearyl alcohol (1-octadecanol); arachidyl alcohol (1-eicosanol); behenyl alcohol (1-docosanol); lignoceryl alcohol (1-tetracosanol); ceryl alcohol (1-hexacosanol); montanyl alcohol (1-octacosanol); myricylic alcohol (1-triacontanol).

Preferably, the solid fatty alcohol is chosen from myristyl alcohol, cetyl alcohol, stearyl alcohol, myristyl alcohol, behenyl alcohol and mixtures thereof such as cetylstearyl or cetearyl alcohol.

In an embodiment, the solid fatty alcohol is chosen from myristyl alcohol.

The liquid fatty alcohols, in particular those containing C10-C34, preferably have branched carbon chains and/or have one or more, preferably 1 to 3 double bonds. They are preferably branched and/or unsaturated (C=C double bond), and contain from 12 to 40 carbon atoms.

The liquid fatty alcohols may be represented by: R—OH, wherein R denotes a C12-C24 branched or straight alkyl group or an alkenyl group, R being optionally substituted by one or more hydroxy groups. Preferably, the liquid fatty alcohol is a branched saturated alcohol. Preferably, R does not contain a hydroxy group. These include oleic alcohol, linoleic alcohol, linolenic alcohol, isocetyl alcohol, isostearyl alcohol, 2-octyl-1-dodecanol, 2-butyloctanol, 2-hexyl-1-decanol, 2-decyl-1-tetradecanol, 2-tetradecyl-1-cetanol and mixtures thereof. Preferably, the liquid fatty alcohol is 2-octyl-1-dodecanol.

In some instances, the compositions include one or more fatty alcohols selected from decyl alcohol, undecyl alcohol, dodecyl alcohol, myristyl alcohol, cetyl alcohol, stearyl alcohol, cetearyl alcohol, isostearyl alcohol, isocetyl alcohol, behenyl alcohol, linalool, oleyl alcohol, myricyl alcohol and a mixture thereof. In some instances, the compositions preferably include myristyl alcohol.

The total amount of the fatty alcohols in the composition, if present, may vary but is typically from about 0.1 to about 15 wt. %, based on the total weight of the composition. In some instances, the total amount of fatty alcohols is from about 0.1 to about 12 wt. %, about 0.1 to about 10 wt. %, about 0.1 to about 8 wt. %, about 0.1 to about 5 wt. %, about 0.5 to about 15 wt. %, about 0.5 to about 12 wt. %, about 0.5 to about 10 wt. %, about 0.5 to about 8 wt. %, or about 0.5 to about 5 wt. %, including ranges and sub-ranges therebetween, based on the total weight of the composition.

In some instances, the compositions of the instant disclosure include at least one fatty ester and at least one fatty alcohol.

In some instances, the compositions of the instant disclosure include at least one glycerol fatty ester and at least one fatty alcohol.

In some instances, the compositions of the instant disclosure include at least one fatty ester, at least one glycerol fatty ester, and at least one fatty alcohol.

In some instances, the fatty ester is a fatty carbonate ester (also referred to as "fatty carbonate"). Accordingly, the compositions may include at least one fatty carbonate, in particular at least one dialkyl carbonate, and at least one fatty alcohol. For example, the composition may include at least one dialkyl carbonate selected from C14-15 dialkyl carbonate, dicaprylyl carbonate, diethyl carbonate, dihexyl carbonate, diethylhexyl carbonate, dimethoxyphenyl phenyloxyethyl ethylcarbonate, dimethyl carbonate, dipropyl carbonate, dipropylheptyl carbonate, dioctyl carbonate, and a mixture thereof; and at least one fatty alcohol selected from decyl alcohol, undecyl alcohol, dodecyl alcohol, myristyl alcohol, cetyl alcohol, stearyl alcohol, isostearyl alcohol, isocetyl alcohol, behenyl alcohol, linalool, and oleyl alcohol. In some cases, the compositions include a combination of dicaprylyl carbonate and myristyl alcohol.

In some cases, the at least one glycerol fatty ester is selected from glyceryl monomyristate, glyceryl monopalmitate, glyceryl monostearate, glyceryl isostearate, glyceryl monooleate, glyceryl dioleate, glyceryl distearate, glyceryl laurate, trilaurin, triarachidin, tribehenin, tricaprin, tricaprylin, caprylic/capric triglyceride, trierucin, triheptanoin, triheptylundecanoin, triisononanoin, triisopalmitin, triisostearin, trilinolein, trimyristin, trioctanoin, triolein, tripalmitin, tripalmitolein, triricinolein, tristearin, triundecanoin, and mixtures thereof. In some cases, the compositions include a combination of caprylic/capric triglyceride and myristyl alcohol.

In some cases, the compositions include a combination of dicaprylyl carbonate, caprylic/capric triglyceride and myristyl alcohol.

One or more thickening agents can optionally be included in the compositions of the instant disclosure. Thickening agents may be referred to as "thickeners" or "viscosity modifying agents." Thickening agents are typically included to increase the viscosity of the compositions. Nonetheless, in some instances, certain thickening agents provide additional, surprising benefits to the compositions. Non-limiting examples of thickening agents include polyacrylate crosspolymers or crosslinked polyacrylate polymers, cationic acrylate copolymers, anionic acrylic or carboxylic acid polymers, polyacrylamide polymers, polysaccharides such as cellulose derivatives, gums, polyquaterniums, vinylpyrrolidone homopolymers/copolymers, C8-24 hydroxyl substituted aliphatic acid, C8-24 conjugated aliphatic acid, sugar fatty esters, polyglyceryl esters, and a mixture thereof. Particular types of thickening agents that may be mentioned include the following:

a. Carboxylic acid or carboxylate based homopolymer or co-polymer, which can be linear or crosslinked: These polymers contain one or more monomers derived from acrylic acid, substituted acrylic acids, and salts and esters of these acrylic acids (acrylates) and the substituted acrylic acids. Commercially available polymers include those sold under the trade names CARBOPOL, ACRYSOL, POLYGEL, SOKALAN, CARBOPOL ULTREZ, and POLYGEL. Examples of commercially available carboxylic acid polymers include the carbomers, which are homopolymers of acrylic acid crosslinked with allyl ethers of sucrose or pentaerytritol. The carbomers are available as the CARBOPOL 900 series from B.F. Goodrich (e.g., CARBOPOL 954). In addition, other suitable carboxylic acid polymeric agents include ULTREZ 10 (B.F. Goodrich) and copolymers of C10-30 alkyl acrylates with one or more monomers of acrylic acid, methacrylic acid, or one of their short chain (i.e., C1-4 alcohol) esters, wherein the crosslinking agent is an allyl ether of sucrose or pentaerytritol. These copolymers are known as acrylates/C10-C30 alkyl acrylate crosspolymers and are commercially available as CARBOPOL 1342, CARBOPOL 1382, PEMULEN TR-1, and PEMULEN TR-2, from B.F. Goodrich.

Other suitable carboxylic acid or carboxylate polymeric agents include copolymers of acrylic acid and alkyl C5-C10 acrylate, copolymers of acrylic acid and maleic anhydride, and polyacrylate crosspolymer-6. Polyacrylate Crosspolymer-6 is available in the raw material known as SEPIMAX ZEN from Seppic.

Another suitable carboxylic acid or carboxylate polymeric agent includes acrylamidopropyltrimonium chloride/acrylates copolymer, a cationic acrylates copolymer (or a quaternary ammonium compound), available as a raw material known under the tradename of SIMULQUAT HC 305 from Seppic.

In certain embodiments, the carboxylic acid or carboxylate polymer thickeners useful herein are those selected from carbomers, acrylates/C10-C30 alkyl acrylate crosspolymers, polyacrylate crosspolymer-6, acrylamidopropyltrimonium chloride/acrylates copolymer, and mixtures thereof.

b. Polyquaternium Compounds: Non-limiting examples, include polyquaternium-1, polyquaternium-2, polyquaternium-3, polyquaternium-4, polyquaternium-5, polyquaternium-6, polyquaternium-7, polyquaternium-8, polyquaternium-9, polyquaternium-10, polyquaternium-11, polyquaternium-12, polyquaternium-13, polyquaternium-14, polyquaternium-15, polyquaternium-16, polyquaternium-17, polyquaternium-18, polyquaternium-19, polyquaternium-20, polyquaternium-21, polyquaternium-22, polyquaternium-23, polyquaternium-24, polyquaternium-25, polyquaternium-26, polyquaternium-27, polyquaternium-28, polyquaternium-29, polyquaternium-30, polyquaternium-40, polyquaternium-41, polyquaternium-42, polyquaternium-43, polyquaternium-44, polyquaternium-45, polyquaternium-46, polyquaternium-47, polyquaternium-48, polyquaternium-49, polyquaternium-50, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-61, polyquaternium-62, polyquaternium-63, polyquaternium-64, polyquaternium-65, polyquaternium-66, polyquaternium-67, etc. In some cases, preferred polyquaternium compounds include polyquaternium-10, polyquaternium-11, polyquaternium-67, and a mixture thereof.

c. Celluloses: Non-limiting examples of celluloses include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. In some instances, the cellulose is selected from water soluble cellulose derivatives (for example, carboxymethyl cellulose, methyl cellulose, methylhydroxypropyl cellulose, hydroxyethyl cellulose, hydroxypropyl cellulose, cellulose sulfate sodium salt). Furthermore, in some instance, the cellulose is preferably hydroxypropylcellulose (HPC).

d. Polyvinylpyrrolidone (PVP) and co-polymers: Non-limiting examples include Polyvinylpyrrolidone (PVP), Polyvinylpyrrolidone (PVP)/vinyl acetate copolymer (PVP/VA copolymer), polyvinylpyrrolidone (PVP)/eicosene copolymer, PVP/hexadecene copolymer, etc. Commercially available polyvinylpyrrolidone includes LUVISKOL K30, K85, K90 available from BASF. Commerically available copolymers of vinylpyrrolidone and vinylacetate include LUVISKOL VA37, VA64 available from BASF; copolymers of vinylpyrrolidone, methacrylamide, and vinylimidazole (INCI: VP/Methacrylamide/Vinyl Imidazole Copolymer) is commercially available as LUVISET from BASF. In some instances, PVP and PVP/VA copolymer are preferred.

e. Sucrose esters: Non-limiting examples include sucrose palmitate, sucrose cocoate, sucrose monooctanoate, sucrose monodecanoate, sucrose mono- or dilaurate, sucrose monomyristate, sucrose mono- or dipalmitate, sucrose mono- and distearate, sucrose mono-, di- or trioleate, sucrose mono- or dilinoleate, sucrose pentaoleate, sucrose hexaoleate, sucrose heptaoleate or sucrose octooleate, and mixed esters, such as sucrose palmitate/stearate, and mixtures thereof.

f. Polyglyceryl esters: Non-limiting polyglycerol esters of fatty acids (polygylceryl esters) include those of the following formula:

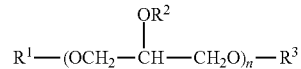

wherein n is from 2 to 20 or from 2 to 10 or from 2 to 5, or is 2, 3, 4, 5, 6, 7, 8, 9, or 10, and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$. Additionally, non-limiting examples of nonionic polyglycerol esters of fatty acids include polyglyceryl-4 caprylate/caprate, polyglyceryl-10 caprylate/caprate, polyglyceryl-4 caprate, polyglyceryl-10 caprate, polyglyceryl-4 laurate, polyglyceryl-5 laurate, polyglyceryl-6 laurate, polyglyceryl-10 laurate, polyglyceryl-10 cocoate, polyglyceryl-10 myristate, polyglyceryl-10 oleate, polyglyceryl-10 stearate, and mixtures thereof.

g. C8-24 hydroxyl substituted aliphatic acid and C8-24 conjugated aliphatic acid: Non-limiting examples include conjugated linoleic acid, cis-parinaric acid, trans-7-octadecenoic acid, cis-5,8,11,14,17-eicosapentanoic acid, cis-4,7,10,13,16,19-docosahexenoic acid, columbinic acid, linolenelaidic acid, ricinolaidic acid, stearidonic acid, 2-hydroxystearic acid, alpha-linolenic acid, arachidonic acid, cis-11,14-eicosadienoic acid, linolelaidic acid, monopetroselinic acid, petroselinic acid, ricinoleic acid, trans-vaccenic acid, cis-11,14,17-eicosatrienoic acid, cis-5-eicosenoic acid, cis-8,11,14-eicosatrienoic acid, hexadecatrienoic acid, palmitoleic acid, petroselaidic acid, trans trans farnesol, cis-13,16-docosadienoic acid, cis-vaccenic acid, cis-11-eicosenoic acid, cis-13,16,19-docosatrienoic acid, cis-13-octadecenoic acid, cis-15-octadecanoic acid, cis-7,10,13,16 docosatetraenoic acid, elaidic acid, gamma-linolenic acid, geranic acid, geranyl geranoic acid, linoleic acid, oleic acid, pinolenic acid, trans-13-octadecenoic acid. More preferably, the aliphatic acid comprises 12-hydroxystearic acid, conjugated linoleic acid, or a mixture thereof.

h. Gums: Non-limiting examples of gums include gum arabic, tragacanth gum, karaya gum, guar gum, gellan gum, tara gum, locust bean gum, tamarind gum, xanthan gum, locust bean gum, Seneca gum, sclerotium gum, gellan gum, etc.

The total amount of thickening agents can vary but is typically from about 0.01 to about 20 wt. %, based on the total weight of the composition. In some instances, the total amount of thickening agents is about 0.01 to about 15 wt. %, about 0.01 to about 10 wt. %, about 0.01 to about 0.01 to about 8 wt. %, about 0.01 to about 6 wt. %, about 0.01 to about 5 wt. %, about 0.1 to about 20 wt. %, about 0.1 to about 15 wt. %, about 0.1 to about 10 wt. %, about 0.1 to about 8 wt. %, about 0.1 to about 6 wt. %, or about 0.1 to about 5 wt. %, including ranges and sub-ranges therebetween, based on the total weight of the composition.

In some instances, the compositions include one or more polyacrylate crosspolymers, for example, polyacrylate crosspolymer-6. The total amount of the polyacrylate crosspolymer(s) can vary but may be from about 0.01 to about 10 wt. %, based on the total weight of the compositions. In some instances, the total amount of polyacrylate crosspolymers is from about 0.01 to about 8 wt. %, about 0.01 to about 5 wt. %, about 0.01 to about 3 wt. %, about 0.1 to about 10 wt. %, about 0.1 to about 8 wt. %, about 0.1 to about 6 wt. %, about 0.1 to about 5 wt. %, or about 0.1 to about 3 wt. %, including ranges and sub-ranges therebetween, based on the total weight of the composition.

In some instances, the compositions include one or more carbomers, which are polymeric materials composed of acrylic acid monomers. The total amount of carbomers may vary but may be from about 0.01 to about 10 wt. %, based on the total weight of the compositions. In some instances, the total amount of carbomers is from about 0.01 to about 8 wt. %, about 0.01 to about 5 wt. %, about 0.01 to about 3 wt. %, about 0.1 to about 10 wt. %, about 0.1 to about 8 wt. %, about 0.1 to about 6 wt. %, about 0.1 to about 5 wt. %, or about 0.1 to about 3 wt. %, including ranges and sub-ranges therebetween, based on the total weight of the composition.

In some instances, the compositions include acrylamidopropyltrimonium chloride/acrylates copolymer, which is a copolymer of one or more of the monomers formed from the amide of acrylic acid, methacrylic acid and aminopropyltrimethyl-ammonium chloride and one or more monomers of acrylic acid, methacrylic acid or one of their esters. The total amount of acrylamidopropyltrimonium chloride/acrylates copolymer may vary but may be from about 0.01 to about 10 wt. %, based on the total weight of the compositions. In some instances, the total amount of acrylamidopropyltrimonium chloride/acrylates copolymer is from about 0.01 to about 8 wt. %, about 0.01 to about 5 wt. %, about 0.01 to about 3 wt. %, about 0.1 to about 10 wt. %, about 0.1 to about 8 wt. %, about 0.1 to about 6 wt. %, about 0.1 to about 5 wt. %, or about 0.1 to about 3 wt. %, including ranges and sub-ranges therebetween, based on the total weight of the composition.

In some instances, the compositions include one or more polyquaternium compounds. Non-limiting examples include polyquaternium-10, polyquaternium-11, and polyquaternium-67. The total amount of polyquaternium compounds may vary but may be from about 0.01 to about 10 wt. %, based on the total weight of the compositions. In some instances, the total amount of polyquaternium compounds is from about 0.01 to about 8 wt. %, about 0.01 to about 5 wt. %, about 0.01 to about 3 wt. %, about 0.1 to about 10 wt. %, about 0.1 to about 8 wt. %, about 0.1 to about 6 wt. %, about 0.1 to about 5 wt. %, or about 0.1 to about 3 wt. %, including ranges and sub-ranges therebetween, based on the total weight of the composition.

In some instances, the compositions include one or more cellulose thickeners (e.g., microcrystalline cellulose, carboxymethylcellulose, hydroxymethylcellulose, and hydroxypropylcellulose). The total amount of cellulose thickeners can vary but may be from about 0.01 to about 10 wt. %, based on the total weight of the compositions. In some instances, the total amount of cellulose thickeners is from about 0.01 to about 8 wt. %, about 0.01 to about 5 wt. %, about 0.01 to about 3 wt. %, about 0.1 to about 10 wt. %, about 0.1 to about 8 wt. %, about 0.1 to about 6 wt. %, about 0.1 to about 5 wt. %, or about 0.1 to about 3 wt. %, including ranges and sub-ranges therebetween, based on the total weight of the composition.

In some instances, the compositions include polyvinylpyrrolidone (PVP) and/or polyvinylpyrrolidone/vinyl acetate (VP/VA) copolymer. The total amount of PVP and/or VP/VA copolymer can vary but may be from about 0.01 to about 10 wt. %, based on the total weight of the compositions. In some instances, the total amount of PVP and/or VP/VA copolymer is from about 0.01 to about 8 wt. %, about 0.01 to about 5 wt. %, about 0.01 to about 3 wt. %, about 0.1 to about 10 wt. %, about 0.1 to about 8 wt. %, about 0.1 to about 6 wt. %, about 0.1 to about 5 wt. %, or about 0.1 to about 3 wt. %, including ranges and sub-ranges therebetween, based on the total weight of the composition.

In some instances, the compositions include one or more C8-24 hydroxyl substituted aliphatic acid, C8-24 conjugated aliphatic acid, or a mixture thereof. A non-limiting but preferred example is hydroxystearic acid. Additional examples include conjugated linoleic acid, cis-parinaric acid, trans-7-octadecenoic acid, cis-5,8,11,14,17-eicosapentanoic acid, cis-4,7,10,13,16,19-docosahexenoic acid, columbinic acid, linolenelaidic acid, ricinolaidic acid, stearidonic acid, 2-hydroxystearic acid, alpha-linolenic acid, arachidonic acid, cis-11,14-eicosadienoic acid, linolelaidic acid, monopetroselinic acid, petroselinic acid, ricinoleic acid, trans-vaccenic acid, and a mixture thereof. Further suitable preferred aliphatic acid include cis-11,14,17-eicosatrienoic acid, cis-5-eicosenoic acid, cis-8,11,14-eicosatrienoic acid, hexadecatrienoic acid, palmitoleic acid, petroselaidic acid, trans trans farnesol, cis-13,16-docosadienoic acid, cis-vaccenic acid, cis-11-eicosenoic acid, cis-13,16,19-docosatrienoic acid, cis-13-octadecenoic acid, cis-15-octadecanoic acid, cis-7,10,13,16 docosatetraenoic acid, elaidic acid, gamma-linolenic acid, geranic acid, geranyl geranoic acid, linoleic acid, oleic acid, pinolenic acid, trans-13-octadecenoic acid. More preferably, the aliphatic acid comprises 12-hydroxystearic acid, conjugated linoleic acid, or a mixture thereof. The total amount of C8-24 hydroxyl substituted aliphatic acid(s) and/or C8-24 conjugated aliphatic acid(s) can vary but may be from about 0.1 to about 20 wt. %, about 0.1 to about 15 wt. %, about 0.1 to about 12 wt. %, about 1 to about 20 wt. %, about 1 to about 15 wt. %, about 1 to about 12 wt. %, about 5 to about 20 wt. %, about 5 to about 15 wt. %, or about 5 to about 12 wt. %, including ranges and sub-ranges therebetween, based on the total weight of the composition.

In some instances, the compositions include one or more sucrose fatty esters. A non-limiting but preferred example is sucrose palmitate. Additional examples include sucrose cocoate, sucrose monooctanoate, sucrose monodecanoate, sucrose mono- or dilaurate, sucrose monomyristate, sucrose mono- or dipalmitate, sucrose mono- and distearate, sucrose mono-, di- or trioleate, sucrose mono- or dilinoleate, sucrose pentaoleate, sucrose hexaoleate, sucrose heptaoleate or sucrose octooleate, and mixed esters, such as sucrose palmitate/stearate. The total amount of sucrose fatty esters can vary but may be from about 0.1 to about 15 wt. %, about 0.1 to about 10 wt. %, about 0.1 to about 8 wt. %, about 1 to about 15 wt. %, about 1 to about 10 wt. %, about 1 to about 8 wt. %, about 2 to about 15 wt. %, about 2 to about 10 wt. %, or about 2 to about 8 wt. %, including ranges and sub-ranges therebetween, based on the total weight of the composition.

In some cases, the compositions are free or essentially free of silicones. For example, the compositions include less than about 3 wt. %, 2 wt. %, 1 wt. %, or 0.5 wt. % of silicones (preferably no silicones). In some cases, the compositions comprise silicones. Non-limiting examples of silicones include amine-functionalized silicones (e.g., amodimethicone), dimethicone, bis-aminopropyl dimethicone, trimethyl silylamodimethicone, etc.

Methods of Treating Hair

The compositions of the instant disclosure are useful for coloring hair, and are also useful for conditioning and/or styling hair. In some instances, when the compositions are applied to wet or damp hair they form a lamellar phase in situ. A "lamellar phase" refers generally to packing of polar-headed long chain nonpolar-tail molecules in an environment of bulk polar liquid (i.e., water from the hair), as sheets of bilayers separated by bulk liquid. The coloring compositions are useful for coloring hair. Such methods include, for example: (i) applying the coloring composition to the hair; (ii) allowing the coloring composition to remain on the hair for a period of time, for example, from about 10 seconds to about 30 minutes; and (iii) rinsing the coloring composition from the hair. The compositions can be applied to the wet or damp hair and may be massaged into the hair, for example, with the hands, and/or spread throughout the hair with a comb or brush. In addition to providing vibrant color to the hair, the methods result in a smoothing and softening of the hair, which reduces frizz, dryness, and unwanted volume.

In addition to the above method steps, aspects of the disclosure are directed to methods of treating hair that include additional steps. For example, when the hair coloring compositions include one or more oxidative dye, the methods typically include the application of a composition containing at least one oxidizing agent (e.g., a developer composition). The hair coloring compositions containing one or more oxidative dyes may optionally include one or more direct dyes. The developer composition may be mixed with the hair coloring composition (e.g., in a 1:1 volumetric ratio) and subsequently applied to dry hair or damp hair. Alternatively, the developer composition may be applied directly to dry hair or damp hair before or after the hair coloring composition is applied to the hair. In other words, the developer composition can be applied to dry or damp hair without being previously mixing the developer composition with a hair coloring composition. Although the amount of hair coloring composition to developer composition may be in a volumetric ratio of 1:1, in some instances the ratio of hair coloring composition to developer composition ranges from 1:5 to 5:1, 1:2 to 2:1, or 1.5:1 to 1:1.5. In at least one preferable embodiment, a developer composition that has not been mixed with a hair coloring composition is applied to hair (either dry or damp hair) before a hair coloring composition is applied to the hair.

The hair is typically rinsed to remove the hair coloring composition and developer composition after about 20 minutes has lapsed. When the developer composition is applied before the hair coloring composition, the hair is typically rinsed about 20 minutes after application of the hair coloring composition. When the hair coloring composition is applied before the developer composition, the hair is typically rinsed about 20 minutes after the application of the developer composition. When the developer composition and the hair coloring composition is mixed prior to application to the hair, the hair is typically rinsed about 20 minutes after the mixture of the developer composition and the hair coloring composition. Although the hair is typically rinsed after 20 minutes has lapsed to remove the hair coloring composition and developer composition, in some instances the hair is rinsed after 5 minutes, after 10 minutes, after 15 minutes, after 25 minutes, after 30 minutes, or after 35 minutes has lapsed.

EMBODIMENTS

In certain embodiments, the compositions of the instant disclosure are substantially anhydrous coloring compositions comprising:
  about 0.01 to about 10 wt. %, preferably about 0.01 to about 5 wt. %, more preferably about 0.1 to about 5 wt. % of one or more colorant comprising at least one of an oxidative dye precursor, a coupler, a direct dye, or a combination thereof, such as one or more direct dyes selected from nitro-phenylenediamines, nitro-aminophenols, azo dyes, anthraquinones, triarylmethane dyes, indophenols, and a mixture thereof and/or one or more oxidative dye precursors selected from ortho aminophenols, para aminophenols, ortho phenylenediamines, para phenylenediamines, double bases, heterocyclic bases, m-aminophenol, 2,4-diaminophenoxyethanol hcl, toluene-2,5-diamine thioglycerin, p-aminophenol, 2-amino-3 hydroxypyridine, 4-amino-2-hydroxytoluene, acid addition salts thereof, or a combination thereof;
  about 20 to about 95 wt. %, preferably about 40 to about 90 wt. %, more preferably about 50 to about 85 wt. % of one or more glycols, for example, one or more glycols selected from ethylene glycol, propylene glycol, butylene glycol, hexylene glycol, pentylene glycol, diethylene glycol, dipropylene glycol, 1,3 propanediol, and glycerin, preferably at least propylene glycol;
  about 5 to about 70 wt. %, preferably about 5 to about 50 wt. %, more preferably about 10 to about 40 wt. % of one or more monoalcohols having from 2 to 6 carbon atoms, preferably ethanol;
    wherein the weight ratio of the glycol(s) to the monoalcohol(s) (glycol(s):monoalcohol(s)) is from 20:1 to 1:1, preferably from 20:1 to 1.1:1, more preferably from 18:1 to 2:1;
  about 0.1 to about 10 wt. %, preferably about 0.1 to about 5 wt. %, more preferably about 0.1 to 2 wt. % of one or more cationic surfactants;
  about 0.1 to about 10 wt. %, preferably about 0.1 to about 5 wt. %, more preferably about 1 to about 0.5 to about 5 wt. % of one or more fatty esters selected from fatty carbonate esters, glycerol fatty esters (glyceryl esters), sucrose fatty esters, sorbitan fatty ester, and fatty acid esters, preferably one or more carbonate esters and/or one or more glycerol fatty esters;

about 0.1 to about 10 wt. %, preferably about 0.1 to about 5 wt. %, more preferably about 0.5 to about 5 wt. % of one or more fatty alcohols selected from cetearyl alcohol, stearyl alcohol, behenyl alcohol, cetyl alcohol, myristyl alcohol, and isostearyl alcohol, preferably myristyl alcohol; and optionally, about 0.1 to about 20 wt. %, preferably about 0.1 to about 15 wt. %, more preferably about 0.1 to about 10 wt. % of one or more thickening agents, for example, one or more thickening agents selected from carboxylic acid or carboxylate based homopolymer or co-polymer, polyquaternium compounds, polyvinylpyrrolidone (PVP) and co-polymers, sucrose esters, polyglyceryl esters, C8-24 hydroxyl substituted aliphatic acid and C8-24 conjugated aliphatic acid, and gums, preferably, polyacrylate crosspolymer, cationic acrylate copolymer, hydroxypropyl cellulose, polyquaterniums, polyvinylpyrrolidone homopolymer/co-polymer, 12-hydroxystearic acid, sugar esters, and polyglyceryl esters;

wherein the composition is a solubilized, non-emulsified composition until applied to the wet or damp hair, whereupon the composition forms a lamellar phase in situ; and all percentages by weight are based on the total weight of the composition.

The cationic surfactants include those described throughout the instant disclosure but may preferably be selected from cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethylamine, behenamidoethyldimethylamine, arachidamidopropyldimethylamine, arachidamido-propyidiethylamine, arachidamidoethyidiethylamine, arachidamidoethyidimethylamine, and mixtures thereof. In some instances, the cationic surfactants are preferably selected from cetrimonium chloride, behentrimonium chloride, behentrimonium methosulfate, stearamidopropyl dimethylamine, and a mixture thereof.

In some instances, the cationic surfactants are more preferably selected from cetrimonium chloride, behentrimonium chloride, behentrimonium methosulfate, stearamidopropyl dimethylamine, and a mixture thereof.

Moreover, in some cases, the cationic surfactant is most preferably cetrimonium chloride, behentrimonium chloride, or a mixture thereof.

In some cases, the compositions are free or essentially free of silicones. For example, the compositions may include less than about 3 wt. %, 2 wt. %, 1 wt. %, or 0.5 wt. % of silicones (preferably no silicones). Non-limiting examples of silicones include amine-functionalized silicones (e.g., amodimethicone), dimethicone, bis-aminopropyl dimethicone, trimethyl silylamodimethicone, etc.

In certain embodiments, the compositions of the instant disclosure are substantially anhydrous cosmetic compositions comprising:

about 0.01 to about 10 wt. %, preferably about 0.01 to about 5 wt. %, more preferably about 0.1 to about 5 wt. % of one or more colorant comprising at least one of an oxidative dye precursor, a coupler, a direct dye, or a combination thereof, such as one or more direct dyes selected from nitro-phenylenediamines, nitro-aminophenols, azo dyes, anthraquinones, triarylmethane dyes, indophenols, and a mixture thereof and/or one or more oxidative dye precursors selected from ortho aminophenols, para aminophenols, ortho phenylenediamines, para phenylenediamines, double bases, heterocyclic bases, m-aminophenol, 2,4-diaminophenoxyethanol hcl, toluene-2,5-diamine thioglycerin, p-aminophenol, 2-amino-3 hydroxypyridine, 4-amino-2-hydroxytoluene, acid addition salts thereof, or a mixture thereof;

about 20 to about 95 wt. %, preferably about 40 to about 90 wt. %, more preferably about 50 to about 85 wt. % of one or more glycols, for example, one or more glycols selected from ethylene glycol, propylene glycol, butylene glycol, hexylene glycol, pentylene glycol, diethylene glycol, dipropylene glycol, 1,3 propanediol, and glycerin, preferably at least propylene glycol;

about 5 to about 70 wt. %, preferably about 5 to about 50 wt. %, more preferably about 10 to about 40 wt. % of ethanol;

wherein the weight ratio of the glycol(s) to the ethanol (glycol(s):ethanol) is from 20:1 to 1:1, preferably from 20:1 to 1.1:1, more preferably from 18:1 to 2:1;

about 0.1 to about 5 wt. %, preferably about 0.1 to about 4 wt. %, more preferably about 0.1 to 2 wt. % of one or more cationic surfactants, for example one or more cationic surfactants selected from cetrimonium chloride, behentrimonium chloride, behentrimonium methosulfate, stearamidopropyl dimethylamine, and a mixture thereof; even more preferably, cetrimonium chloride, behentrimonium chloride, or a mixture thereof;

about 0.1 to about 10 wt. %, preferably 0.1 to about 5 wt. %, more preferably about 0.5 to about 5 wt. % of one or more fatty esters including:

(i) fatty carbonate esters selected from dialkyl carbonates of formula: $R_1O(C=O)R_2$, wherein $R_1$ and $R_2$ are independently linear or branched, saturated or unsaturated alkyl chains having 1 to 30 carbon atoms, or having 2 to 28 carbon atoms, or having 4 to 25 carbon atoms, or having 6 to 22 carbon atoms, preferably one or more dialkyl fatty carbonates selected from C14-15 dialkyl carbonate, dicaprylyl carbonate, diethyl carbonate, dihexyl carbonate, diethylhexyl carbonate, dimethoxyphenyl phenyloxoethyl ethylcarbonate, dimethyl carbonate, dipropyl carbonate, dipropylheptyl carbonate, dioctyl carbonate, and a mixture thereof; and/or (ii) glycerol fatty esters selected from glyceryl caprate, glyceryl caprylate, glyceryl oleate, glyceryl linoleate, glyceryl myristate, glyceryl capromyristate, glyceryl stearate, glyceryl hydroxy stearate, glyceryl isostearate, glyceryl ricinoleate, glyceryl dilaurate, glyceryl dioleate, glyceryldistearate, glycerylmono/dicaprylate, glycerylmono/dimyristate, glycerylstearatepalmitate, glyceryltricaprate/caprylate, caprylic/capricdiglycerylsuccinate, caprylic/capric glycerides, caprylic/capric/isostearic/adipictriglycerides, caprylic/capric/linoleictriglycerides, caprylic/caprictriglycerides, caprylic/capric/stearictriglycerides, glyceryltrilaurate/stearate, glyceryldi/tripalmitostearate, glyceryldi/tritristearate, caprylictriglyceride, caprylic/capric/laurictriglycerides, glyceryltriheptanoate, glyceryl trioctanoate, glyceryl trilaurate, glyceryl trioleate, glyceryltristearate, glyceryltris-12-hydroxystearate, glyceryltriacetyl hydroxystearate, glyceryl tri acetyl ricinioleate, glyceryl triisostearate, glyceryl tribehenate, and mixtures thereof;

about 0.1 to about 10 wt. %, preferably about 0.1 to about 5 wt. %, more preferably about 0.5 to about 5 wt. % of one or more fatty alcohols selected from cetearyl alcohol, stearyl alcohol, behenyl alcohol, cetyl alcohol, myristyl alcohol, isostearyl alcohol, and a mixture thereof; and optionally, about 0.1 to about 20 wt. %, preferably about 0.1 to about 15 wt. %, more preferably about 0.1 to about 10 wt. % of one or more thickening agents, for example, one or more thickening agents selected from carboxylic acid or carboxylate based homopolymer or co-polymer, polyquaternium compounds, polyvinylpyrrolidone (PVP) and co-polymers, sucrose esters, polyglyceryl esters, C8-24 hydroxyl substituted aliphatic acid and C8-24 conjugated aliphatic acid, and gums, preferably, polyacrylate crosspolymer, cationic acrylate copolymer, hydroxypropyl cellulose, polyquaterniums, polyvinylpyrrolidone homopolymer/co-polymer, 12-hydroxystearic acid, sugar esters, and polyglycery esters;

wherein the composition is a solubilized, non-emulsified composition until applied to the wet or damp hair, whereupon the composition forms a lamellar phase in situ; and all percentages by weight are based on the total weight of the composition.

In some cases, the compositions are free or essentially free of silicones. For example, the compositions may include less than about 3 wt. %, 2 wt. %, 1 wt. %, or 0.5 wt. % of silicones (preferably no silicones). Non-limiting examples of silicones include amine-functionalized silicones (e.g., amodimethicone), dimethicone, bis-aminopropyl dimethicone, trimethylsilylamodimethicone, etc.

Direct Dyes

Examples of suitable direct dyes that may be mentioned include azo direct dyes; anthraquinone and anthraquinone derivatives; (poly)methine dyes such as cyanins, hemicyanins and styryls; carbonyl dyes; azine dyes; nitro(hetero)aryl dyes; tri(hetero)arylmethane dyes; porphyrin dyes; phthalocyanin dyes, and natural direct dyes, alone or as mixtures. The direct dyes may be cationic or anionic.

Many direct dyes are cationic direct dyes. Mention may be made of the hydrazono cationic dyes of formulas (Va) and (V'a), the azo cationic dyes (VIa) and (VI'a) and the diazo cationic dyes (VIIa) below:

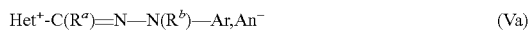   (Va)

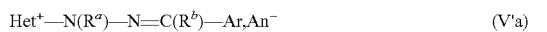   (V'a)

   (VIa)

   (VI'a)

and

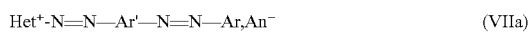   (VIIa)

in which formulas (Va), (V'a), (VIa), (VI'a) and (VIIa):

Het$^+$ represents a cationic heteroaryl radical, preferably bearing an endocyclic cationic charge, such as imidazolium, indolium or pyridinium, optionally substituted preferentially with one or more $(C_1\text{-}C_8)$alkyl groups such as methyl;

Ar$^+$ representing an aryl radical, such as phenyl or naphthyl, bearing an exocyclic cationic charge, preferentially ammonium, particularly tri$(C_1\text{-}C_8)$alkylammonium such as trimethylammonium;

Ar represents an aryl group, especially phenyl, which is optionally substituted, preferentially with one or more electron-donating groups such as i) optionally substituted $(C_1\text{-}C_8)$alkyl, ii) optionally substituted $(C_1\text{-}C_8)$ alkoxy, iii) (di)$(C_1\text{-}C_8)$(alkyl)amino optionally substituted on the alkyl group(s) with a hydroxyl group, iv) aryl$(C_1\text{-}C_8)$alkylamino, v) optionally substituted N—$(C_1\text{-}C_8)$alkyl-N-aryl$(C_1\text{-}C_8)$alkylamino or alternatively Ar represents a julolidine group;

Ar' is an optionally substituted divalent (hetero)arylene group such as phenylene, particularly para-phenylene, or naphthalene, which are optionally substituted, preferentially with one or more groups $(C_1\text{-}C_8)$alkyl, hydroxyl or $(C_1\text{-}C_8)$alkoxy Ar" is an optionally substituted (hetero)aryl group such as phenyl or pyrazolyl, which are optionally substituted, preferentially with one or more groups $(C_1\text{-}C_8)$alkyl, hydroxyl, (di)$(C_1\text{-}C_8)$(alkyl)amino, $(C_1\text{-}C_8)$alkoxy or phenyl;

$R^a$ and $R^b$, which may be identical or different, represent a hydrogen atom or a group $(C_1\text{-}C_8)$alkyl, which is optionally substituted, preferentially with a hydroxyl group;

or alternatively the substituent $R^a$ with a substituent of Het$^+$ and/or $R_b$ with a substituent of Ar and/or $R^a$ with $R_b$ form, together with the atoms that bear them, a (hetero)cycloalkyl;

particularly, $R^a$ and $R_b$ represent a hydrogen atom or a group $(C_1\text{-}C_4)$alkyl, which is optionally substituted with a hydroxyl group;

An$^-$ represents an anionic counter-ion such as mesylate or halide. In particular, mention may be made of the azo and hydrazono cationic dyes bearing an endocyclic cationic charge of formulae (Va), (V'a) and (VIa) as defined previously. More particularly those of formulae (Va), (V'a) and (VIa) derived from the dyes described in patent applications WO 95/15144, WO 95/01772 and EP-714954, which are incorporated herein by reference in their entirety.

In some cases, the cationic part is derived from the following derivatives:

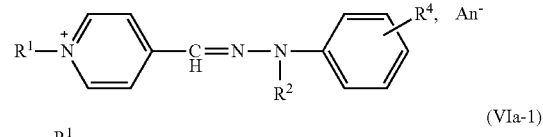

(Va-1)

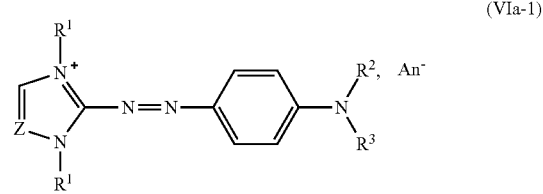

(VIa-1)

formulae (V-1) and (VI-1) with:

$R^1$ representing a $(C_1\text{-}C_4)$alkyl group such as methyl;

$R^2$ and $R^3$, which are identical or different, represent a hydrogen atom or a $(C_1\text{-}C_4)$alkyl group, such as methyl; and $R^4$ represents a hydrogen atom or an electron-donating group such as optionally substituted $(C_1\text{-}C_8)$alkyl, optionally substituted $(C_1\text{-}C_8)$alkoxy, or (di)$(C_1\text{-}C_8)$ (alkyl)amino optionally substituted on the alkyl group(s) with a hydroxyl group; particularly, $R^4$ is a hydrogen atom, Z represents a CH group or a nitrogen atom, preferentially CH;

An⁻ represents an anionic counter-ion such as mesylate or halide.

Particularly, the dye of formulae (Va-1) and (VIa-1) is chosen from Basic Red 51, Basic Yellow 87 and Basic Orange 31 or derivatives thereof:

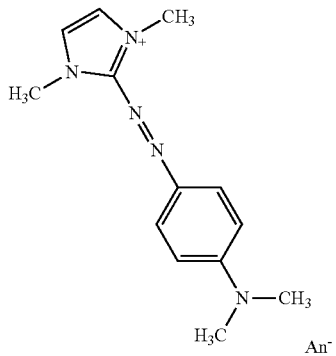

Basic Red 51

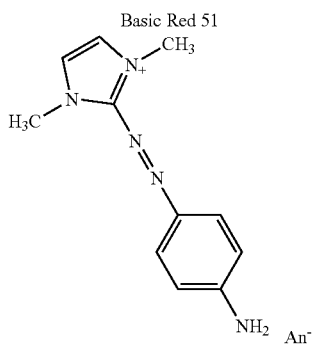

Basic Orange 31

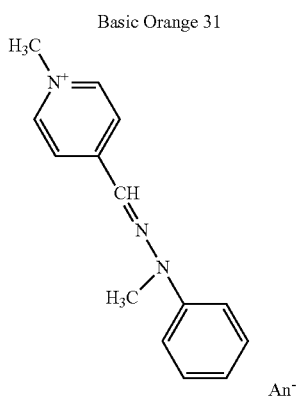

Basic Yellow 87

Non-limiting examples of cationic dyes include Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green, Basic Orange 31, 1, Basic Red 2, Basic Red 12 Basic Red 22, Basic Red 76 Basic Red 51, Basic Violet 1, Basic Violet 2, Basic Violet 3, Basic Violet 10, Basic Violet 14, Basic Yellow 57 and Basic Yellow 87.

Non-limiting examples anionic dyes include Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2 (Ext Violet 2), D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium and/or potassium.

Non-limiting examples of nitro dyes include HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Blue No. 17, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

The total amount of direct dyes in compositions may vary but is typically from about 0.001 to about 10 wt. %, based on the total weight of the composition. In some cases, the total amount of direct dyes in the composition may be from about 0.001 to about 8 wt. %, about 0.001 to about 6 wt. %, about 0.001 to about 5 wt. %, about 0.001 to about 4 wt. %, about 0.001 to about 3 wt. %, about 0.01 to about 10 wt. %, about 0.01 to about 8 wt. %, about 0.01 to about 6 wt. %, about 0.01 to about 5 wt. %, about 0.01 to about 4 wt. %, about 0.01 to about 3 wt. %, about 0.1 to about 10 wt. %, about 0.1 to about 8 wt. %, about 0.1 to about 6 wt. %, or about 0.1 to about 5 wt. %, about 0.1 to about 4 wt. %, or about 0.1 to about 3 wt. %, based on the total weight of the composition.

Oxidative Dye Precursors

The hair coloring compositions may include at least one oxidative dye precursors as a colorant. The oxidative dye of the present disclosure may be selected from any type of oxidative dye useful for imparting color to hair. The oxidative dye may also encompass a wide variety of oxidation dye precursors. These include primary dye intermediates and couplers.

Primary Dye Intermediates

Examples of primary dye intermediates include ortho or para aminophenols, ortho or para phenylenediamines, double bases, heterocyclic bases, and the acid addition salts thereof.

The para-phenylenediamines which can be used include compounds of the following formula (XIV) and their addition salts with an acid:

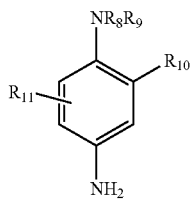

(XIV)

in which:
R$_8$ represents a hydrogen atom, a C$_1$-C$_4$ alkyl radical, a C$_1$-C$_4$ monohydroxyalkyl radical, a C$_2$-C$_4$ polyhydroxyalkyl radical, a (C$_1$-C$_4$)alkoxy(C$_1$-C$_4$)alkyl radical, a C$_1$-C$_4$ alkyl radical substituted by a nitrogenous group, a phenyl radical or a 4'-aminophenyl radical;
R$_9$ represents a hydrogen atom, a C$_1$-C$_4$ alkyl radical, a C$_1$-C$_4$ monohydroxyalkyl radical, a C$_2$-C$_4$ polyhydroxyalkyl radical, a (C$_1$-C$_4$)alkoxy(C$_1$-C$_4$)alkyl radical or a C$_1$-C$_4$ radical substituted by a nitrogenous group;
R$_8$ and R$_9$ can also form, with the nitrogen atom which carries them, a 5- or 6-membered nitrogenous heterocycle optionally substituted by one or more alkyl, hydroxyl or ureido groups;
R$_{10}$ represents a hydrogen atom, a halogen atom, such as a chlorine atom, a C$_1$-C$_4$ alkyl radical, a sulpho radical, a carboxyl radical, a C$_1$-C$_4$ monohydroxyalkyl radical, a C$_1$-C$_4$ hydroxyalkoxy radical, a C$_1$-C$_4$ acetylaminoalkoxy radical, a C$_1$-C$_4$ mesylaminoalkoxy radical or C$_1$-C$_4$ carbamoylaminoalkoxy radicals;
R$_{11}$ represents a hydrogen atom, a halogen atom or a C$_1$-C$_4$ alkyl radical.

The nitrogenous groups in the above formula (XIV) include amino, mono(C$_1$-C$_4$)alkylamino, di(C$_1$-C$_4$)alkylamino, tri(C$_1$-C$_4$)alkylamino, monohydroxy(C$_1$-C$_4$)alkylamino, imidazolinium and ammonium radicals.

The para-phenylenediamines of above formula (XIV) include para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(p-hydroxyethyl)amino-2-chloroaniline, 2-(β-hydroxyethyl)-para-phenylenediamine, 2-fluoro-para-phenylenediamine, 2-isopropyl-para-phenylenediamine, N-(13-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-(β-hydroxyethyloxy)-para-phenylenediamine, 2-(β-acetylaminoethyloxy)-para-phenylenediamine, N-(β-methoxyethyl)-para-phenylenediamine, 2-methyl-1-N-(β-hydroxyethyl)-para-phenylenediamine and their addition salts with an acid.

In one embodiment, the para-phenylenediamines of above formula (XIV) include para-phenylenediamine, para-toluylenediamine, 2-isopropyl-para-phenylenediamine, 2-(β-hydroxyethyl)-para-phenylenediamine, 2-(β-hydroxyethyloxy)-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and their addition salts with an acid.

The ortho-phenylenediamines include N1-(2-hydroxyethyl)-4-nitro-o-phenylenediamine, 4-methyl-o-phenylenediamine, and 4-nitro-o-phenylenediamine and acid addition salts thereof.

As used herein, the term "double bases" means compounds comprising at least two aromatic nuclei having at least one of amino and hydroxyl groups.

Examples include compounds corresponding to the following formula (XV) and their addition salts with an acid:

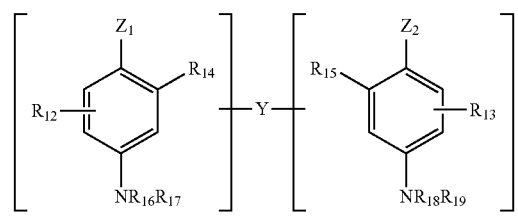

(XV)

in which:
Z$_1$ and Z$_2$, which are identical or different, represent a hydroxyl or —NH$_2$ radical which can be substituted by a C$_1$-C$_4$ alkyl radical or by a connecting arm Y;
the connecting arm Y represents a linear or branched alkylene chain comprising from 1 to 14 carbon atoms which can be interrupted or terminated by one or more nitrogenous groups and/or by one or more heteroatoms, such as oxygen, sulphur or nitrogen atoms, and which is optionally substituted by one or more hydroxyl or C$_1$-C$_6$ alkoxy radicals;
R$_{12}$ and R$_{13}$ represent a hydrogen or halogen atom, a C$_1$-C$_4$ alkyl radical, a C$_1$-C$_4$ monohydroxyalkyl radical, a C$_2$-C$_4$ polyhydroxyalkyl radical, a C$_1$-C$_4$ aminoalkyl radical or a connecting arm Y;
R$_{14}$, R$_{15}$, R$_{16}$, R$_{17}$, R$_{18}$ and R$_{19}$, which are identical or different, represent a hydrogen atom, a connecting arm Y or a C$_1$-C$_4$ alkyl radical;
it being understood that the compounds of formula (XV) only comprise a single connecting arm Y per molecule.

Nitrogenous groups of the above formula (XV) include amino, mono(C1-C4)alkylamino, di(C1-C4)alkylamino, tri(C1-C4)alkylamino, monohydroxy(C1-C4)alkylamino, imidazolinium and ammonium radicals.

Additional examples of double bases of above formula (XV) include of N,N'-bis(p-hydroxyethyl)-N,N'-bis(4'-aminophenyl)-1,3-diamino-propanol, N,N'-bis(β-hydroxyethyl)-N,N'-bis(4'-aminophenyl)ethylenediamine, N,N'-bis(4-aminophenyl)-tetramethylenediamine, N,N'-bis(β-hydroxyethyl)-N,N'-bis(4-amino-phenyl)tetramethylenediamine, N,N'-bis(4-methylaminophenyl)tetramethylenediamine, N,N'-diethyl-N,N'-bis(4'-amino-3'-methylphenyl)ethylenediamine, 1,8-bis(2,5-diamino-phenoxy)-3,5-dioxaoctane and their addition salts with an acid.

In one embodiment the double base is N,N'-Bis(β-hydroxyethyl)-N,N'-bis(4'-aminophenyl)-1,3-diaminopropanol, 1,8-bis(2,5-diaminophenoxy)-3,5-dioxaoctane or one of their addition salts with an acid.

The para-aminophenols which can be used include compounds of the following formula (XVI) and their addition salts with an acid:

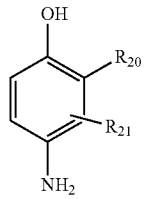

(XVI)

in which:
R$_{20}$ represents a hydrogen atom, a halogen atom, such as fluorine, a C$_1$-C$_4$ alkyl radical, a C$_1$-C$_4$ monohydroxyalkyl radical, a (C$_1$-C$_4$)alkoxy(C$_1$-C$_4$)alkyl radical, a C$_1$-C$_4$ aminoalkyl radical or a hydroxy(C$_1$-C$_4$)alkylamino-(C$_1$-C$_4$)alkyl radical,
R$_{21}$ represents a hydrogen atom, a halogen atom, such as fluorine, a C$_1$-C$_4$ alkyl radical, a C$_1$-C$_4$ monohydroxyalkyl radical, a C$_2$-C$_4$ polyhydroxyalkyl radical, a C$_1$-C$_4$ aminoalkyl radical, a C$_1$-C$_4$ cyanoalkyl radical or a (C$_1$-C$_4$)alkoxy(C$_1$-C$_4$)alkyl radical. Among the para-aminophenols, mention may be made of para-aminophenol, 4-amino-3-methylphenol, 4-amino-3-fluorophenol, 4-amino-3-hydroxymethylphenol, 4-amino-2-methylphenol, 4-amino-2-hydroxymethyl phenol, 4-amino-2-methoxymethylphenol, 4-amino-2-aminomethylphenol, 4-amino-2-(β-hydroxyethylaminomethyl)phenol, N-methyl-para-aminophenol, and the acid addition salts thereof.

The ortho-aminophenols that may be used as oxidation bases in the context of certain embodiments may be chosen from 2-aminophenol, 2-amino-1-hydroxy-5-methylbenzene, 2-amino-1-hydroxy-6-methylbenzene, 5-acetamido-2-aminophenol, and the acid addition salts thereof.

Heterocyclic bases that can be used as oxidation bases in the methods of coloring keratinous fibers include pyridine derivatives, pyrimidine derivatives, pyrazole derivatives, pyrazolinone derivatives, and the acid addition salts thereof.

Pyridine derivatives include the compounds described, for example, in patents GB 1,026,978 and GB 1,153,196, as well as the compounds 2,5-diaminopyridine, 2-(4-methoxyphenyl)amino-3-aminopyridine, 2,3-diamino-6-methoxypyridine, 2-(β-methoxyethyl)amino-3-amino-6 methoxypyridine, 3,4-diaminopyridine, and the acid addition salts thereof.

Pyrimidine derivatives include the compounds disclosed, for example, in German Patent DE 2 359 399 or Japanese Patents JP 88-169 571 and JP 91-10659 or Patent Application WO 96/15765, such as 2,4,5,6-tetra-aminopyrimidine, 4-hydroxy-2,5,6-triaminopyrimidine, 2-hydroxy-4,5,6-triamino-pyrimidine, 2,4-dihydroxy-5,6-diaminopyrimidine, 2,5,6-triaminopyrimidine, and the pyrazolopyrimidine derivatives, such as those mentioned in French Application FR-A-2 750 048 and among which may be mentioned pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo [1,5-a]pyrimidin-7-ylamino)ethanol; 2-(7-aminopyrazolo[1,5-a]pyrimidin-3-ylamino)ethanol; 2-[(3-aminopyrazolo[1,5-a]pyrimidin-7-yl)(2-hydroxyethyl)amino]ethanol; 2-[(7-aminopyrazolo[1,5-a]pyrimidin-3-yl)(2-hydroxyethyl) amino]ethanol; 5,6-dimethyl-pyrazolo[1,5-a]pyrimidine-3,7-diamine; 2,6-dimethylpyrazolo[1,5-a]pyrimidine-3,7-diamine; 2,5,N7,N7-tetramethylpyrazolo[1,5-a]pyrimidine-3,7-diamine; 3-amino-5-methyl-7-(imidazolylpropylamino) pyrazolo[1,5-a]pyrimidine; and their addition salts and their tautomeric forms, when there exists a tautomeric equilibrium, and their addition salts with an acid.

Pyrazole and pyrazolinone derivatives include the compounds described in patents DE 3,843,892, DE 4,133,957 and patent applications WO 94/08969, WO 94/08970, FR-A-2,733,749, and DE 195 43 988, such as 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1, 3-dimethyl-5-hydrazinopyrazole, 1-benzyl-4,5-diamino-3-methylpyrazole, 4, 5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-(β-hydroxyethyppyrazole, 4,5-diamino-1-ethyl-3-methylpyrazole, 4,5-diamino-1-ethyl-3-(4'-methoxyphenyl) pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl) amino-1,3-dimethyl-pyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl) amino-1-methylpyrazole, 2-(4,5-diamino-1H-pyrazol-1-yl), H$_2$SO$_4$, 2,3-diamino-6,7-dihydro-1H,5H-pyrazolo[1,2-z] pyrazol-1-one, 1-methyl-3-phenyl-2-pyrazolinone, and the acid addition salts thereof.

Primary intermediates include p-phenylenediamine, p-aminophenol, o-aminophenol, N,N-bis(β-hydroxyethyl)-p-phenylenediamine, 2, 5-diaminotoluene, their salts and mixtures thereof.

The primary intermediates may be employed in amounts ranging from 0.0001% to 12% by weight, or from 0.0001% to 8.0% by weight, or, from 0.005% to 5% by weight, based on the total weight of the coloring composition.

Coupler(s)

The hair coloring composition according to the present disclosure may optionally comprise one or more couplers advantageously chosen from those conventionally used in the dyeing or coloring of keratin fibers. The couplers that may be used in the dyeing method disclosed herein include those conventionally used in oxidative methods of coloring keratinous fibers, for example, meta-aminophenols, meta-phenylenediamines and meta-diphenols, naphthols, mono- or polyhydroxylated naphthalene derivatives, and heterocyclic couplers such as, for example, indole derivatives, indoline derivatives, sesamol and its derivatives, pyridine derivatives, pyrazolotriazole derivatives, pyrazolones, indazoles, benzimidazoles, benzothiazoles, benzoxazoles, 1,3-benzodioxoles, quinolines, benzomorpholine derivatives, pyrazoloazole derivatives, pyrroloazole derivatives, imidazoloazole derivatives, pyrazolopyrimidine derivatives, pyrazoline-3,5-dione derivatives, pyrrolo[3,2-d]oxazole derivatives, pyrazolo[3,4-d]thiazole derivatives, thiazoloazole S-oxide derivatives, thiazoloazole S,S-dioxide derivatives, and the acid addition salts thereof. Among these couplers, mention may be made especially of meta-phenylenediamines, meta-aminophenols, meta-diphenols, naphthalene-based couplers and heterocyclic couplers, and also the addition salts thereof.

Mention may be made, for example, of 2-methyl-5-aminophenol, 5-N-(β-hydroxyethyl)amino-2-methylphenol, 3-aminophenol, 5-amino-6-chloro-o-cresol (3-amino-2-chloro-6-methylphenol), 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diamino-phenoxy)propane, 3-ureidoaniline, 3-ureido-1-dimethylamino-benzene, sesamol, 1-β-hydroxyethylamino-3,4-methylene-dioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylene-dioxybenzene, 2,6-bis(J-hydroxyethylamino)toluene, 6-hydroxy-indoline, 2,6-dihydroxy-4-methylpyridine, 1-H-3-methylpyrazol-5-one, 1-phenyl-3-methylpyrazol-5-one, 2,6-dimethyl-pyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof.

Suitable color couplers include, for example, those having the general formula (XVII):

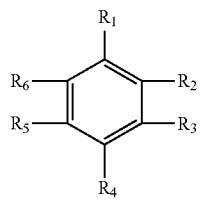

(XVII)

wherein $R_1$ is unsubstituted hydroxy or amino, or hydroxy or amino substituted with one or more $C_{1-6}$ hydroxyalkyl groups, $R_3$ and $R_5$ are each independently hydrogen, hydroxy, amino, or amino substituted with $C_{1-6}$ alkyl, $C_{1-6}$ alkoxy, or $C_{1-6}$ hydroxyalkyl group; and $R_2$, $R_4$, and $R_6$ are each independently hydrogen, $C_{1-6}$ alkoxy, $C_{1-6}$ hydroxyalkyl, or $C_{1-6}$ alkyl, or $R_3$ and $R_4$ together may form a methylenedioxy or ethylenedioxy group. Examples of such compounds include meta-derivatives such as phenols, meta-aminophenols, meta-phenylenediamines, and the like, which may be unsubstituted, or substituted on the amino group or benzene ring with alkyl, hydroxyalkyl, alkylamino groups, and the like. Suitable couplers include m-aminophenol, 2,4-diaminotoluene, 4-amino, 2-hydroxytoluene, phenyl methyl pyrazolone, 3,4-methylenedioxyphenol, 3,4-methylenedioxy-1-[(beta-hydroxyethyl)amino]benzene, 1-methoxy-2-amino-4-[(beta-hydroxyethyl)amino]benzene, 1-hydroxy-3-(dimethylamino)benzene, 6-methyl-1-hydroxy-3[(beta-hydroxyethypamino]penzene, 2,4-dichloro-1-hydroxy-3-aminobenzene, 1-hydroxy-3-(diethylamino)benzene, 1-hydroxy-2-methyl-3-aminobenzene, 2-chloro-6-methyl-1-hydroxy-3-aminobenzene, 1,3-diaminobenzene, 6-methoxy-1,3-diaminobenzene, 6-hydroxyethoxy-1,3-diaminobenzene, 6-methoxy-5-ethyl-1,3-diaminobenzene, 6-ethoxy-1,3-diaminobenzene, 1-bis(beta-hydroxyethyl)amino-3-aminobenzene, 2-methyl-1, 3-diaminobenzene, 6-methoxy-1-amino-3-[(beta-hydroxyethyl)amino]-benzene, 6-(beta-aminoethoxy)-1,3-diaminobenzene, 6-(beta-hydroxyethoxy)-1-amino-3-(methylamino)benzene, 6-carboxymethoxy-1,3-diaminobenzene, 6-ethoxy-1-bis(beta-hydroxyethyl)amino-3-aminobenzene, 6-hydroxyethyl-1,3-diaminobenzene, 1-hydroxy-2-isopropyl-5-methylbenzene, 1,3-dihydroxybenzene, 2-chloro-1,3-dihydroxybenzene, 2-methyl-1,3-dihydroxybenzene, 4-chloro-1,3-dihydroxybenzene, 5,6-dichloro-2-methyl-1, 3-dihydroxybenzene, 1-hydroxy-3-amino-benzene, 1-hydroxy-3-(carbamoylmethylamino)benzene, 6-hydroxybenzomorpholine, 4-methyl-2,6-dihydroxypyridine, 2,6-dihydroxypyridine, 2,6-diaminopyridine, 6-aminobenzomorpholine, 1-phenyl-3-methyl-5-pyrazolone, 1-hydroxynaphthalene, 1,7-dihydroxynaphthalene, 1,5-dihydroxynaphthalene, 5-amino-2-methyl phenol, 4-hydroxyindole, 4-hydroxyindoline, 6-hydroxyindole, 6-hydroxyindoline, 2,4-diamionphenoxyethanol, and mixtures thereof.

Other couplers may be chosen, for example, from 2,4-diamino-1-(β-hydroxyethyloxy)benzene, 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino 1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, 1-amino-2-methoxy-4,5-methylenedioxybenzene, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, 2-amino-3-hydroxypyridine, 3,6-dimethylpyrazolo[3,2-c]-1,2,4-triazole, 2, 6-dimethylpyrazolo[1,5-b]-1,2,4-triazole, 6-methyl pyrazolo[1,5-a]-benzimidazole, and the acid addition salts thereof.

In one embodiment, the couplers include resorcinol, 1-naphthol, 2-methylresorcinol, 4-amino-2-hydroxy toluene, m-aminophenol, 2,4-diaminophenoxyethanol, phenyl methyl pyrazolone, hydroxybenzomorpholine, 2-methyl-5-hydroxyetyylaminophenol, 6-hydroxyindole, 2-amino-3-hydroxypyridine, 5-amino-6-chloro-o-cresol, 4-chlororesorcinol, their salts, and mixtures thereof.

In general, the addition salts of the oxidation bases and couplers that may be used in the context of the disclosure are especially selected from the addition salts with an acid such as the hydrochlorides, hydrobromides, sulfates, citrates, succinates, tartrates, lactates, tosylates, benzenesulfonates, phosphates and acetates.

The oxidation base(s) each advantageously represent from 0.001% to 10% by weight relative to the total weight of the coloring composition or kits thereof, and preferably from 0.005% to 5% by weight relative to the total weight of the coloring compositions or kits thereof of the present disclosure. The coupler(s), if they are present, each advantageously represent from 0.001% to 10% by weight relative to the total weight of the coloring composition or kits thereof, and preferably from 0.005% to 5% by weight relative to the total weight of the compositions or kits thereof of the present disclosure.

Oxidizing Agents

The hair coloring compositions, or kits thereof, may include at least one oxidizing agent. The oxidizing agents may be selected from, for example, peroxides, persulfates, perborates percarbonates, alkali metal bromates, ferricyanides, peroxygenated salts, or a mixture thereof. Oxidizing agents that may also be used include at least one redox enzyme such as laccases, peroxidases, and 2-electron oxidoreductases, such as uricase, where appropriate in the presence of their respective donor or co-factor. Oxygen in the air may also be employed as an oxidizing agent.

In some cases, the oxidizing agent is a persulfate and/or a monopersulfate such as, for example, potassium persulfate, sodium persulfate, ammonium persulfate, as well as mixtures thereof. In one embodiment, the oxidizing agents in the present disclosure are selected from hydrogen peroxide, potassium persulfate, sodium persulfate, and mixtures thereof.

One or more oxidizing agents are typically included in an oxidizing composition (may also be known as developer composition). An oxidizing composition may be a hair lightening or bleaching composition or it may be a neutralizing composition or a developer composition. In some cases, the total amount of the one or more oxidizing agents in an oxidizing composition is essentially 100% (as is the case for some powdered oxidation compositions). In some cases, the total amount of the one or more oxidizing agents is about 1 to about 80 wt. %, about 1 to about 70 wt. %, about 1 to about 60 wt. %, about 1 to about 50 wt. %, about 1 to about 40 wt. %, about 5 to about 80 wt. %, about 5 to about 70 wt. %, about 5 to about 60 wt. %, about 5 to about 50 wt. %, about 5 to about 40 wt. %, about 10 to about 80 wt. %, about 10 to about 70 wt. %, about 10 to about 60 wt. %, about 10 to about 50 wt. %, or about 10 to about 40 wt. %, based on the total weight of the coloring composition.

Reducing Agents

The hair coloring compositions, or kits thereof, may include one or more reducing agents. Typical reducing agents are capable of reducing the disulfide bonds in the hair to produce free thiol groups. The reducing agent preferably comprises one or more thiol (SH) groups. Compounds containing thiol groups are known in other applications to be cosmetically acceptable for application to the hair. Suitable reducing agents include, for example, compounds containing from 1 to 6 carbon atoms and one or more other functional groups such as hydroxyl and carboxylate, e.g., dithiothreitol, thioglycolate and mixtures thereof.

Non-limiting examples of reducing agents include thioglycolic acid and thioglycolic acid salts and esters, thiolactic acid and thiolactic acid salts and esters, cysteine thioglycerol, thioglycolic hydrazide, thioglycolamide, glycerol monothioglycolate, sodium metabisulfite, beta-mercaptopropionic acid, N-hydroxyethyl mercapto-acetamide, N-methyl mercapto-acetamide, beta-mercapto-ethylamine, beta-mercaptopropionamide, 2-mercapto-ethanesulfonic acid, dimercaptoadipic acid, dithiothreitol, homocysteinethiolactone, cysteine derivatives, polythiol derivatives formed by the addition of cysteamine onto a maleic anhydride-alkylvinylether copolymer, inorganic sulfites, inorganic bisulfites, cysteamine and its derivatives, dithioerythritol, organic phosphines, and mixtures thereof.

A non-exausitive list of reducing agents is as follows: Mercapto-carboxylic Acids (e.g. 2-mercaptopropionic acid, 3-mercaptopropionic acid, mercaptosuccinic acid, thioglycolic acid, ammonium thioglycollate, sodium thioglycollate, L-cysteine, Di-mercapto-adipic acid); Mercapto-amines (e.g. L-cysteine, ethyl ester, L-cysteine methyl ester, N-acetyl-L-cysteine, cysteamine); Mercapto-amides (e.g. thioglycolamide, N-hydroxyethyl mercapto-acetamide, N-methyl mercapto acetamide, 2-mercaptopropionamide); Sulphites (e.g. ammonium bisulphite, sodium bisulphite, ammonium sulphite, sodium sulphite); hydroxides (e.g. guanidine hydroxide, sodium hydroxide); Alcohols and Diols (e.g. resorcinol, thioglycerol, glycerol monothioglycollate, glycol thioglycolate); Di-thio compounds (e.g. dihydrolipoic acid, sodium dihydrolipoate, dithiothreitol, 1,3-dithiopropanol); Others (e.g. lithium chloride, tris(hydroxymethyl) phosphine, cuprar.-monium hydroxide, thioglycolic hydrazide, 2-mercapto-ethanesulphonic acid, homocysteine thiolactone, polythiol polymers, salts of hydrogen sulphide, amines in alkaline solution, salts of hydrogen cyanide, borohydride, dithionite, ester salts of sulphoxylate).

One or more reducing agents may be included in reducing compositions. The total amount of the one or more reducing agents can vary, but in some cases, the total amount of the one or more reducing agents is about 0.1 to about 25 wt. %, about 0.1 to about 20 wt. %, about 0.1 to about 15 wt. %, 0.1 to about 10 wt. %, 0.1 to about 5 wt. %, about 1 to about 25 wt. %, about 1 to about 20 wt. %, about 1 to about 15 wt. %, about 1 to about 10 wt. %, or about 1 to about 5 wt. %, based on the total weight of the composition.

Non-Reducing Agents for Shaping Hair

The hair coloring compositions, or kits thereof, may include one or more non-reducing agents for shaping hair. The non-reducing agents for shaping hair may be one or more hydroxide compounds, non-hydroxide compounds, or mixtures thereof. For instance, the hydroxide compounds may be alkali metal hydroxides, alkaline-earth metal hydroxides, transition metal hydroxides, and mixtures thereof. Non-limiting examples include of hydroxide compounds include sodium hydroxide, potassium hydroxide, lithium hydroxide, calcium hydroxide, magnesium hydroxide, barium hydroxide, strontium hydroxide, manganese hydroxide, zinc hydroxide, guanidine hydroxide, and mixtures thereof.

Neutralizing Agents

The hair coloring compositions, or kits thereof, may include neutralizing agents. In some cases, after treating hair with hair coloring compositions, or kits thereof, of the present disclosure comprising active agents chosen from reducing agents for curling or shaping the hair (as in perming and hair straightening systems), the hair is treated with a neutralizing agent or composition containing a neutralizing agent. For instance, the neutralizing agent may be an oxidizing agent chosen from hydrogen peroxide, urea hydrogen peroxide, alkali metal bromates, or persalts, such as perborates and persulphates. One or more neutralizing agents may be included in neutralizing compositions. The total amount of the one or more neutralizing agents can vary, but in some cases, the total amount of the one or more neutralizing agents is about 0.1 to about 25 wt. %, about 0.1 to about 20 wt. %, about 0.1 to about 15 wt. %, 0.1 to about 10 wt. %, 0.1 to about 5 wt. %, about 1 to about 25 wt. %, about 1 to about 20 wt. %, about 1 to about 15 wt. %, about 1 to about 10 wt. %, or about 1 to about 5 wt. %, based on the total weight of the composition.

Cationic Surfactants

Non-limiting examples of cationic surfactants include behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride (Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, and hexadecyltrimethyl ammonium bromide.

The cationic surfactant(s) may also be chosen from optionally polyoxyalkylenated, primary, secondary or tertiary fatty amines, or salts thereof, and quaternary ammonium salts, and mixtures thereof.

In some cases it is useful to use salts such as chloride salts of the quaternary ammonium compounds.

The fatty amines generally comprise at least one $C_8$-$C_{30}$ hydrocarbon-based chain.

A. Examples of quaternary ammonium salts that may especially be mentioned include: those corresponding to the general formula (III) below:

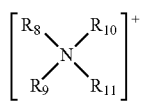

(III)

in which the groups $R_8$ to $R_{11}$, which may be identical or different, represent a linear or branched, saturated or unsaturated aliphatic group comprising from 1 to 30 carbon atoms, or an aromatic group such as aryl or alkylaryl, at least one of the groups $R_8$ to $R_{11}$ denoting a group comprising from 8 to 30 carbon atoms and preferably from 12 to 24 carbon atoms. The aliphatic groups may comprise heteroatoms especially such as oxygen, nitrogen, sulfur and halogens. The aliphatic groups are chosen, for example, from $C_1$-$C_{30}$ alkyl, $C_2$-$C_{30}$ alkenyl, $C_1$-$C_{30}$ alkoxy, polyoxy($C_2$-$C_6$)alkylene, $C_1$-$C_{30}$ alkylamide, ($C_{12}$-$C_{22}$)alkylamido($C_2$-$C_6$)alkyl, ($C_{12}$-$C_{22}$)alkyl acetate and $C_1$-$C_{30}$ hydroxyalkyl groups; X is an anion chosen from the group of halides, phosphates, acetates, lactates, ($C_1$-$C_4$)alkyl sulfates, and ($C_1$-$C_4$)alkyl- or ($C_1$-$C_4$)alkylarylsulfonates.

Among the quaternary ammonium salts of formula (III), those that are preferred are, on the one hand, tetraalkylammonium salts, for instance dialkyldimethylammonium or alkyltrimethylammonium salts in which the alkyl group contains approximately from 12 to 22 carbon atoms, in particular behenyltrimethylammonium, distearyldimethylammonium, cetyltrimethylammonium or benzyldimethylstearylammonium salts, or, on the other hand, oleocetyldimethylhydroxyethylammonium salts, palmitylamidopropyltrimethylammonium salts, stearamidopropyltrimethylammonium salts and stearamidopropyldimethylcetearylammonium salts.

B. a quaternary ammonium salt of imidazoline, such as, for example, those of formula (IV) below:

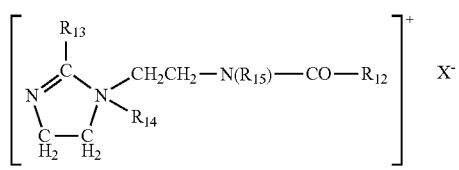

(IV)

in which $R_{12}$ represents an alkenyl or alkyl group comprising from 8 to 30 carbon atoms, derived for example from tallow fatty acids, $R_{13}$ represents a hydrogen atom, a $C_1$-$C_4$alkyl group or an alkyl or alkenyl group comprising from 8 to 30 carbon atoms, $R_{14}$ represents a $C_1$-$C_4$alkyl group, $R_{15}$ represents a hydrogen atom or a $C_1$-$C_4$alkyl group, $X^-$ is an anion chosen from the group of halides, phosphates, acetates, lactates, alkyl sulfates, alkyl- or alkylaryl-sulfonates in which the alkyl and aryl groups preferably comprise, respectively, from 1 to 20 carbon atoms and from 6 to 30 carbon atoms. $R_{12}$ and $R_{13}$ preferably denote a mixture of alkenyl or alkyl groups containing from 12 to 21 carbon atoms, derived for example from tallow fatty acids, $R_{14}$ preferably denotes a methyl group, and $R_{15}$ preferably denotes a hydrogen atom. Such a product is sold, for example, under the name REWOQUAT W 75 by the company Rewo;

C. a quaternary diammonium or triammonium salt, in particular of formula (V):

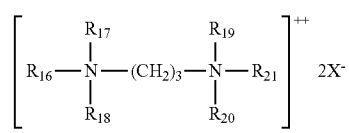

(V)

in which $R_{16}$ denotes an alkyl radical comprising approximately from 16 to 30 carbon atoms, which is optionally hydroxylated and/or interrupted with one or more oxygen atoms, $R_{17}$ is chosen from hydrogen or an alkyl radical comprising from 1 to 4 carbon atoms or a group ($R_{16a}$)($R_{17a}$)($R_{18a}$)N—(CH$_2$)$_3$, $R_{16a}$, $R_{17a}$, $R_{18a}$, $R_{18}$, $R_{19}$, $R_{20}$ and $R_{21}$, which may be identical or different, being chosen from hydrogen and an alkyl radical comprising from 1 to 4 carbon atoms, and $X^-$ is an anion chosen from the group of halides, acetates, phosphates, nitrates and methyl sulfates. Such compounds are, for example, Finquat CT-P, sold by the company Finetex (Quaternium 89), and Finquat CT, sold by the company Finetex (Quaternium 75), D. Cationic/cationizable surfactants, for example of the general structure

R4-A-R5-B wherein R4 is a saturated or unsaturated, straight or branched alkyl chain with 8 to 24 C atoms, R5 is a straight or branched alkyl chain with 1 to 4 C atoms, A is selected from:

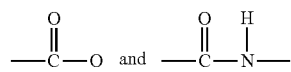

and B is selected from

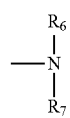

wherein $R_6$ and $R_7$ are the same or different is H or an alkyl chain with 1 to 4 C atoms, hydroxyl alkyl chain with 1 to 4 C atoms and di hydroxyl alkyl chain with 2 to 4 C atoms,

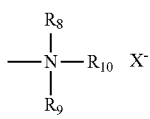

$R_8$ and $R_9$ are the same or different, an alkyl chain with 1 to 4 C atoms, hydroxyl alkyl chain with 1 to 4 C atoms and di hydroxyl alkyl chain with 2 to 4 C atoms, $R_{10}$ is an alkyl chain with 1 to 4 C atoms, hydroxyl alkyl chain with 1 to 4 C atoms or di hydroxyl alkyl chain with 2 to 4 C atoms.

In some instances, $R_4$ is saturated or unsaturated, straight or branched alkyl chain with 10 to 24C atoms, more preferably 12 to 22 C atoms and $R_5$ is straight or branched alkyl group with 1 to 4 C atoms, and A, B, $R_6$ to $R_{10}$ are same as above.

Non-limiting suitable examples are stearyloxypropyl amine, palmityloxypropyl amine, stearyloxypropyldimethyl amine, stearyloxypropyldiethyl amine, stearyloxyethylyldimethyl amine, stearyloxyethyl amine, myristyloxypropyl amine, myristyloxypropyldimethyl amine, palmitamidopropyl amine, palmitamidopropyl methylamine, palmitamidopropyl diethylamine, palmitamidopropyl dibutylamine, palmitamidopropyl buylamine, palmitamidopropyl dipropylamine, palmitamidopropyl propylamine, palmitamidopropyl dihydroxyethylamine, palmitamidopropyl hydroxyethylamine, palmitamidopropyl dihydroxypropylamine, palmitamidopropyl hydroxypropylamine, lauramidopropyl amine, lauramidopropyl methylamine, lauramidopropyl diethylamine, lauramidopropyl dibutylamine, lauramidopropyl buylamine, lauramidopropyl dipropylamine, lauramidopropyl propylamine, lauramidopropyl dihydroxyethylamine, lauramidopropyl hydroxyethylamine, lauramidopropyl dihydroxypropylamine, lauramidopropyl hydroxypropylamine, stearamidopropyl amine, stearamidopropyl dimethylamine, steara midopropyl diethylamine, stearamidopropyldibutylamine, stearamidopropyl butylamine, stearamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, behenamidopropyl amine, behenamidopropyl methylamine, behenamidopropyl diethylamine, behenamidopropyl dibutylamine, behenamidopropyl butylamine, behenamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, dipalmitamidopropyl methylamine, dipalmitamidopropyl ethylamine, dipalmitamidopropyl butylamine, dipalmitamidopropyl propylamine, dipalmitamidopropyl hydroxyethylamine, dipalmitamidopropyl hydroxypropylamine, dilauramidopropyl amine, dilauramidopropyl methylamine, dilauramidopropyl buylamine, dilauramidopropyl hydroxyethylamine, dilauramidopropyl hydroxypropylamine, distearamidopropyl amine, distearamidopropyl methylamine, dibehenamidopropyl propylamine, dibehenamidopropyl hydroxyethylamine, palmitoamidopropyl trimethyl ammonium chloride, stearamidopropyl trimethylammonium chloride, behenamidopropyl tri hydroxyethalmonium chloride, distearylamidopropyl dimethyl ammonium chloride, dicetylamidodihydroxyethyl ammonium chloride, palmitoylpropyl amine, palmitoylpropyl methylamine, palmitoylpropyl diethylamine, palmitoylpropyl dibutylamine, palmitoylpropyl buylamine, palmitoylpropyl dipropylamine, palmitoylpropyl propylamine, palmitoylpropyl dihydroxyethylamine, palmitoylpropyl hydroxyethylamine, palmitoylpropyl dihydroxypropylamine, palmitoylpropyl hydroxypropylamine, myristoylpropyl amine, myristoylpropyl methylamine, myristoylpropyl diethylamine, myristoylpropyl dibutylamine, myristoylpropyl buylamine, myristoylpropyl dipropylamine, myristoylpropyl propylamine, myristoylpropyl dihydroxyethylamine, myristoylpropyl hydroxyethylamine, myristoylpropyl dihydroxypropylamine, myristoylpropyl hydroxypropylamine, stearoylpropyl amine, stearoylpropyl methylamine, stearoylpropyl diethylamine, stearoylpropyl dibutylamine, stearoylpropyl butylamine, stearoylpropyl dipropylamine, behenylpropyl propylamine, behenylpropyl dihydroxyethylamine, behenylpropyl hydroxyethylamine, behenylpropyl dihydroxypropylamine, behenylpropyl hydroxypropylamine, behenylpropyl amine, behenylpropyl methylamine, behenylpropyl diethylamine, behenylpropyl dibutylamine, behenylpropyl butylamine, behenylpropyl dipropylamine, behenylpropyl propylamine, behenylpropyl dihydroxyethylamine, behenylpropyl hydroxyethylamine, behenylpropyl dihydroxypropylamine, behenylpropyl hydroxypropylamine, dipalmitoylpropyl methylamine, dipalmitoylpropyl ethylamine, dipalmitylpropyl butylamine, dipalmitylpropyl propylamine, dipalmitylpropyl hydroxyethylamine, dipalmitylpropyl hydroxypropylamine, dilauroylpropyl amine, dilauroylpropyl methylamine, dilauroylpropyl buylamine, dilauroylpropyl hydroxyethylamine, dilauroylpropyl hydroxypropylamine, distearylpropyl amine, distearylpropyl methylamine, dibehenylpropyl propylamine, dibehenylpropyl hydroxyethylamine, palmitylpropyl trimethyl ammonium chloride, stearylpropyl trimethylammonium chloride, behenylpropyl tri hydroxyethalmonium chloride, distearylpropyl dimethyl ammonium chloride, dicetyldihydroxyethyl ammonium chloride, dioleoylethylhydroxyethylmonium methosulfate, and dicocoylethylhydroxyethylmonium methosulfate.

Cationizable surfactants or amphiphilic surfactants may be chosen from fatty alkylamines, preferably, fatty dialkylamines. In some cases, the fatty dialkylamines may be fatty dimethylamines. Non-limiting examples include dimethyl lauramine, dimethyl behenamine, dimethyl cocamine, dimethyl myristamine, dimethyl palmitamine, dimethyl stearamine, dimethyl tallowamine, dimethyl soyamine, and mixtures thereof.

Fatty dialkylamines include fatty amidoamine compounds, their salts, and mixtures thereof. Non-limiting examples include oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethylamine, behenamidoethyldimethylamine, arachidamidopropyldimethylamine, arachidamido-propyidiethylamine, arachidamidoethyidiethylamine, arachidamidoethyidimethylamine, brassicamidopropyldimethylamine, lauramidopropyl dimethylamine, myristamidopropyl dimethylamine, dilinoleamidopropyl dimethylamine, and palmitamidopropyl dimethylamine.

In some cases the compositions of the instant disclosure include at least one cationic surfactant selected from stearamidopropyl dimethylamine.

Non-polymeric, mono-, di-, and/or tri-carboxylic acids may be used to "neutralize" the fatty dialkylamines. In some cases, the one or more non-polymeric, mono-, di-, and/or tri-carboxylic acids include at least one dicarboxylic acid. Non-limiting examples include lactic acid, oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, 2,6-naphthalene dicarboxylic acid, benzoic acid, and mixtures thereof. In particular, lactic acid or tartaric acid or mixtures thereof are useful, especially in combination with fatty dimethylamines such as, for example, stearamidopropyl dimethylamine.

Fatty Compounds

A "fatty compound" is an organic compound that is not soluble in water at normal temperature (25° C.) and at atmospheric pressure (750 mmHg) (solubility below 10%). In some instances, the solubility in water may be below 5%, below 1%, or below 0.1%). Moreover, fatty compounds are generally soluble in one or more organic solvents under the same conditions of temperature and pressure, for example organic solvents such as chloroform, ethanol, benzene or decamethylcyclopentasiloxane.

Non-limiting examples of fatty compounds include oils, mineral oil, fatty alcohols, fatty acids, fatty alcohol derivatives, fatty acid derivatives (such as alkoxylated fatty acids or polyethylene glycol esters of fatty acids or propylene glycol esters of fatty acids or butylene glycol esters of fatty acids or esters of neopentyl glycol and fatty acids or polyglycerol/glycerol esters of fatty acids or glycol diesters or diesters of ethylene glycol and fatty acids or esters of fatty acids and fatty alcohols, esters of short chain alcohols and fatty acids), esters of fatty alcohols, hydroxy-substituted fatty acids, waxes, triglyceride compounds, lanolin, and a mixture thereof. In some instances, the at least one fatty compound includes one or more fatty alcohols, fatty acids, esters of fatty acids, and/or esters of fatty alcohols (for example, cetyl palmitate, cetyl stearate, myristyl myristate, myristyl stearate, cetyl myristate, and stearyl stearate (a mixture of which is referred to as "cetyl esters")).

Fatty compounds include hydrocarbons, fatty alcohols, fatty alcohol derivatives, fatty acids, fatty acid derivatives, fatty esters, fatty ethers, oils, waxes, etc. The fatty compounds may be liquid or solid at room temperature and at atmospheric pressure (25° C., 1 atm). Non-limiting examples of the fatty alcohols, fatty acids, fatty alcohol derivatives, and fatty acid derivatives are found in International Cosmetic Ingredient Dictionary, Sixteenth Edition, 2016, which is incorporated by reference herein in its entirety.

Non-limiting examples of hydrocarbons include linear or branched, optionally cyclic $C_6$-$C_{16}$ alkanes; hexane, undecane, dodecane, tridecane, and isoparaffins, for instance isohexadecane, isododecane and isodecane. Additionally, the linear or branched hydrocarbons may be composed only of carbon and hydrogen atoms of mineral, plant, animal or synthetic origin with more than 16 carbon atoms, such as volatile or non-volatile liquid paraffins, petroleum jelly, liquid petroleum jelly, polydecenes, hydrogenated polyisobutene, and squalane.

The fatty alcohols that can be used may be liquid at 25° C., 1 atm, or may even be solid. They may even be glycerolated and/or oxyalkylenated, and may include from 8 to 30 carbon atoms. They may be saturated or unsaturated. The fatty alcohols useful herein include those having from about 8 to about 30 carbon atoms, from about 12 to about 22 carbon atoms, and from about 14 to about 22 carbon atoms. These fatty alcohols can be straight or branched chain alcohols and can be saturated or unsaturated. Nonlimiting examples of fatty alcohols include decyl alcohol, undecyl alcohol, dodecyl alcohol, myristyl alcohol, cetyl alcohol, stearyl alcohol, isostearyl alcohol, isocetyl alcohol, behenyl alcohol, linalool, oleyl alcohol, cholesterol, cis4-t-butylcyclohexanol, myricyl alcohol and a mixture thereof. In some cases, the fatty alcohols are those selected from the group consisting of myristyl alcohol, cetyl alcohol, stearyl alcohol, isostearyl alcohol, oleyl alcohol, isotridecyl alcohol, and a mixture thereof.

The saturated liquid fatty alcohols may be branched. They can optionally comprise, in their structure, at least one aromatic or non-aromatic ring, but are preferably acyclic. Non-limiting examples of liquid saturated fatty alcohols include octyldodecanol, isostearyl alcohol, and 2-hexyldecanol.

The unsaturated liquid fatty alcohols include in their structure at least one double or triple bond and preferably one or more double bonds. When several double bonds are present, there are preferably 2 or 3 of them and they can be conjugated or non-conjugated. These unsaturated fatty alcohols can be linear or branched. They can optionally include in their structure at least one aromatic or non-aromatic ring but they are preferably acyclic. Among liquid unsaturated fatty alcohols, oleyl alcohol, linoleyl alcohol, linolenyl alcohol and undecylenyl alcohol can be cited.

Non-limiting examples of solid fatty alcohols include linear or branched, saturated or unsaturated alcohols containing from 8 to 30 carbon atoms, for example, myristyl alcohol, cetyl alcohol, stearyl alcohol and their mixture, cetylstearyl alcohol.

Non-limiting examples of liquid fatty esters include esters from a $C_6$-$C_{32}$ fatty acid and/or a $C_6$-$C_{32}$ fatty alcohol, and are liquid at 25° C., 1 atm. These esters may be liquid esters of saturated or unsaturated, linear or branched $C_1$-$C_{26}$ aliphatic mono or polyacids and of saturated or unsaturated, linear or branched $C_1$-$C_{25}$ aliphatic mono or polyalcohols, the total number of carbon atoms in the esters being greater than or equal to 10. In some cases, for the esters of monoalcohols, at least one of the alcohol or the acid from which the esters of the invention result is branched. Among the monoesters of monoacids and of monoalcohols, mention may be made of ethyl palmitate, isopropyl palmitate, alkyl myristates such as isopropyl myristate or ethyl myristate, isocetyl stearate, 2-ethylhexyl isononanoate, isononyl isononanoate, isodecyl neopentanoate and isostearyl neopentanoate.

In some cases, it is particularly useful to include cetyl esters in the hair conditioning compositions. Cetyl Esters is a mixture of the following esters of saturated fatty acids and fatty alcohols: cetyl palmitate, cetyl stearate, myristyl myristate, myristyl stearate, cetyl myristate, and stearyl stearate.

Fatty alcohol derivatives include alkyl ethers of fatty alcohols, alkoxylated fatty alcohols, alkyl ethers of alkoxylated fatty alcohols, esters of fatty alcohols and a mixture thereof. Nonlimiting examples of fatty alcohol derivatives include materials such as methyl stearyl ether; 2-ethylhexyl dodecyl ether; stearyl acetate; cetyl propionate; the ceteth series of compounds such as ceteth-1 through ceteth-45, which are ethylene glycol ethers of cetyl alcochol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; C1-C30 alkyl ethers of the ceteth, steareth, and ceteareth compounds just described;

polyoxyethylene ethers of branched alcohols such as octyldodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG8-ceteth-1, and PPG-10 cetyl ether; and a mixture thereof.

Esters of $C_4$-$C_{22}$ dicarboxylic or tricarboxylic acids and of $C_1$-$C_{22}$ alcohols and esters of monocarboxylic, dicarboxylic or tricarboxylic acids and of $C_4$-$C_{26}$ dihydroxy, trihydroxy, tetrahydroxy or pentahydroxy non-sugar alcohols may also be used. Mention may be made in particular of diethyl sebacate; diisopropyl sebacate; diisopropyl adipate; di-n-propyl adipate; triisopropyl citrate; glyceryl trilactate; glyceryl trioctanoate; neopentyl glycol diheptanoate; and diethylene glycol diisononanoate.

As oils of plant origin or synthetic triglycerides that may be used in the composition of the invention as liquid fatty esters, the following can be cited, for example, triglyceride oils of plant or synthetic origin, such as liquid fatty acid triglycerides containing from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, castor oil, avocado oil, olive oil, rapeseed oil, coconut oil, wheatgerm oil, sweet almond oil, apricot oil, safflower oil, candlenut oil, coconut oil, camellina oil, tamanu oil, babassu oil and pracaxi oil, jojoba oil, and shea butter oil.

The solid fatty acid esters and/or fatty acid esters that may be mentioned include solid esters obtained from $C_9$-$C_{26}$ fatty acids and from $C_9$-$C_{25}$ fatty alcohols. Among these esters, mention may be made of octyldodecyl behenate, isocetyl behenate, cetyl lactate, stearyl octanoate, octyl octanoate, cetyl octanoate, decyl oleate, myristyl stearate, octyl palmitate, octyl pelargonate, octyl stearate, alkyl myristates such as cetyl myristate, myristyl myristate or stearyl myristate, and hexyl stearate.

The liquid fatty ethers may be chosen from liquid dialkyl ethers such as dicaprylyl ether. The non-liquid fatty ethers may also be chosen from dialkyl ethers and in particular dicetyl ether and distearyl ether, alone or as a mixture.

Non-limiting examples of waxes include carnauba wax, candelilla wax, esparto wax, paraffin wax, ozokerite, plant waxes such as olive tree wax, rice wax, hydrogenated jojoba wax or absolute flower waxes, such as the blackcurrant blossom essential wax sold by Bertin (France), or animal waxes such as beeswaxes or modified beeswaxes (cerabellina), and ceramides. Non-limiting examples of ceramides include N-linoleyldihydrosphingosine, N-oleyldihydrosphingosine, N-palmityldihydrosphingosine, N-stearyldihydrosphingosine or N-behenyldihydrosphingosine, or mixtures of these compounds.

The fatty acid derivatives are defined herein to include fatty acid esters of the fatty alcohols as defined above, fatty acid esters of the fatty alcohol derivatives as defined above when such fatty alcohol derivatives have an esterifiable hydroxyl group, fatty acid esters of alcohols other than the fatty alcohols and the fatty alcohol derivatives described above, hydroxy-substituted fatty acids, and a mixture thereof. Nonlimiting examples of fatty acid derivatives include ricinoleic acid, glycerol monostearate, 12-hydroxy stearic acid, ethyl stearate, cetyl stearate, cetyl palmitate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, and a mixture thereof.

In some cases, the one or more fatty compounds may be one or more high melting point fatty compounds. A high melting point fatty compound is a fatty compound having a melting point of greater than 25° C. Even higher melting point fatty compounds may also be used, for example, fatty compounds having a melting point of 30° C. or higher, 40° C. or higher, 45° C. or higher, 50° C. or higher. The high melting point fatty compound may be selected from the group consisting of fatty alcohols, fatty acids, fatty alcohol derivatives, fatty acid derivatives, and mixtures thereof. Non-limiting examples of the high melting point compounds are found in International Cosmetic Ingredient Dictionary, Fifteenth Edition, 2014, which is incorporated herein by reference in its entirety. The fatty alcohols useful herein are those having from about 12 to about 30 carbon atoms, preferably from about 14 to about 22 carbon atoms. These fatty alcohols are saturated and can be straight or branched chain alcohols. Non-limiting examples of high melting point fatty compounds include fatty alcohols such as, for example, myristyl alcohol (having a melting point of about 38° C.), cetyl alcohol (having a melting point of about 56° C.), stearyl alcohol (having a melting point of about 58-59° C.), behenyl alcohol (having a melting point of about 71° C.), and mixtures thereof. These compounds are known to have the above melting points. However, they often have lower melting points when supplied, since such supplied products are often mixtures of fatty alcohols having alkyl chain length distribution in which the main alkyl chain is cetyl, stearyl or behenyl group. In the present application, more preferred fatty alcohols are myristyl alcohol, cetyl alcohol, stearyl alcohol and mixtures thereof.

In an embodiment, the fatty alcohol in the compositions of the present disclosure comprises myristyl alcohol.

Kits

According to another aspect of the disclosure, a kit is provided comprising a hair coloring composition as discussed herein, and optionally one or more of a developer composition, a reducing composition, a neutralizing composition, and/or a developer composition, where each of the foregoing compositions is contained separately. The developer composition may be in the form of a powder, gel, liquid, foam, lotion, cream, mousse, and emulsion. Optionally, water may be added as an activator, by mixing it with the developer composition.

Developer compositions often include oxidizing agents, such as a peroxide (e.g. hydrogen peroxide). Suitable oxidizing agents include any of the oxidizing agents discussed above. The developer composition may also optionally comprise a cosmetically acceptable carrier. The hydrogen peroxide may be present in an amount of at least about 1% by weight, based on the total weight of the developer composition. In some cases, hydrogen peroxide is present in an amount ranging from about 0.1% to about 80% by weight, such as from about 1.0% to about 75% by weight, or from about 2% to about 10% by weight, including subranges thereof, based on the total weight of the developer composition. Furthermore, the hydrogen peroxide may be present in the developer composition in an amount ranging from about 2% to about 25%, such as about 4% to about 20%, about 6% to about 15%, or about 7% to about 10%, including subranges thereof, based on the total weight of the developer composition.

The cosmetically acceptable carrier of the developer composition may, for example, be present in an amount ranging from about 0.5% to about 99% by weight, such as from about 5% to about 95% by weight, including subranges thereof, relative to the total weight of the developer composition.

The pH of the developer composition can range from about 1 to about 5, such as from about 2 to about 4, and it may be adjusted to the desired value using pH adjusters that are well known in the art in the cosmetic treatment of keratin fibers, including, for example, those described herein.

The developer composition may, in various cases, comprise additional components such as, for example, at least one auxiliary ingredient chosen from rheology-modifying agents, chelants, fatty substances, ceramides, alkoxyamino-silicones, and silanes, and any other component known in the art to be useful in a developer composition.

In some instances, the bleach composition and developer composition may be combined to form the lightening composition or color-altering composition in a ratio of bleach composition to developer composition ranging from about 1:1 to about 1:5, such as from about 1:1 to about 1:2, or about 1:2 to about 1:4.

Additionally, one or more components of the hair coloring compositions discussed above may be provided as a separately contained composition as part of a kit. For example, a kit may comprise a hair coloring composition as discussed above, optionally a reducing compositions, optionally a neutralizing composition, and/or optionally a developer composition.

Implementation of the present disclosure is provided by way of the following examples. The examples serve to illustrate the technology without being limiting in nature.

Example 1

Composition with Anionic Direct Dyes

|  | INCI US | A wt. % | B wt. % | C wt. % | D wt. % | E wt. % |
|---|---|---|---|---|---|---|
| Direct Dye (Anionic) | EXT. VIOLET 2 | 0.5 | 0.4 |  | 0.5 | 0.5 |
|  | RED 40 |  |  | 0.4 |  |  |
| Mono-Alcohol | ETHANOL AND/OR ISOPROPYL ALCOHOL | 20 | 20 | 20 | 10 | 10 |
| PG | PROPYLENE GLYCOL | 74.1 | 74.2 | 74.2 | 82.2 | 82 |
|  | Ratio PG/EtOH | 3.7 | 3.7 | 3.7 | 8.2 | 8.2 |
| Cationic Surfactant | CETRIMONIUM CHLORIDE AND/OR | 1.2 | 1.2 | 1.2 | 0.6 | 0.6 |
| Fatty Ester | DICAPRYLYL CARBONATE | 0.9 | 0.9 | 0.9 | 0.9 | 0.9 |
| Fatty Alcohol | MYRISTYL ALCOHOL | 2 | 2 | 2 | 2 | 2 |
| Thickening agent | HYDROXYPROPYLCELLULOSE VP/VA COPOLYMER |  |  |  | 1 | 0.2 1 |
| Misc. | PRESERVATIVES, FRAGRANCE, SALTS, pH ADJUSTERS, ETC. | ≤2 | ≤2 | ≤2 | ≤2 | ≤2 |
| Water | WATER | 0.1 | 0.1 | 0.1 | 1.8 | 1.8 |

Example 2

Composition with Cationic Direct Dyes

|  | INCI US | F wt. % | G wt. % | H wt. % |
|---|---|---|---|---|
| Direct Dye (Cationic) | BASIC RED 51 | 0.1 | 0.04 |  |
|  | BASIC ORANGE |  |  | 0.1 |
| Mono-Alcohol | ETHANOL | 28.6 | 28.7 | 28.6 |
| PG | PROPYLENE GLYCOL | 65 | 65 | 65 |
|  | Ratio PG/EtOH | 2.3 | 2.3 |  |
| Cationic Surfactant | CETRIMONIUM CHLORIDE | 0.6 | 0.6 | 0.6 |
| Fatty Alcohol | MYRISTYL ALCOHOL | 2 | 2 | 2 |
| Fatty Ester | DICAPRYLYL CARBONATE | 0.9 | 0.9 | 0.9 |
| Misc. | PRESERVATIVES, FRAGRANCE, SALTS, pH ADJUSTERS, ETC. | ≤2 | ≤2 | ≤2 |
| Water | WATER | 1.8 | 1.8 | 1.8 |

Example 3

Color Deposition of Anionic Direct Dyes

Testing was carried out to determine the color deposition provided using anionic direct dyes. The base composition of Composition B was used and different amounts of direct dye (Ext. Violet 2) was added at 0.1 wt. %, 0.25 wt. %, 0.4 wt. %, and 0.5 wt. % was added, based on the total weight of the final coloring composition. Separately, two comparative compositions were made by adding 0.5 wt. % of the Ext. Violet 2 to water and by adding 0.5 wt. % of the Ext. Violet 2 to an organic solvent (80/20 propylene glycol to ethanol). Finally, hair swatches were treated with a commercial conditioner containing direct dyes. The formulation of the commercial conditioner is provided below.

| Commercial Conditioner | INCI US | wt. % |
|---|---|---|
| Direct Dye (anionic) | EXT. VIOLET 2 | 0.5 |
| Cationic Surfactant | CETRIMONIUM CHLORIDE | 0.8 |

| Commercial Conditioner | INCI US | wt. % |
| --- | --- | --- |
| Fatty Acid | CETEARYL ALCOHOL | 9.1 |
| Hair Conditioning Agent | DIPALMITOYLETHYL HYDROXYETHYLMONIUM METHOSULFATE | 1.4 |
| Emollient | CETYL ESTERS | 1 |
| Oil | MINERAL OIL & SOYBEAN OIL | 2 |
| Misc. | PRESERVATIVES, FRAGRANCE, SALTS, pH ADJUSTERS, UV FILTERS, ETC. | ≤2 |
| Water | WATER | QS 100 |

The resulting coloring compositions were used to treat bleached hair swatches and the treated hair swatches where then evaluated using the CIE L*a*b* system using a Minolta Spectrophotometer CM3600D colorimeter.

In the L*a*b* system, the three parameters simply denote, respectively, the color intensity (L*), the green/red color axis (a*) and the blue/yellow color axis (b*). The L*a*b* colorimetric system is a colorimetric system that assigns each color to a position in a spherical color space. The brightness is represented by a position in the ordinate (z-axis) direction, the hue is represented by a position in the circumferential direction, and the chroma is represented by a distance from the center axis. The position on the ordinate (z-axis) representing brightness is designated by L*, and the L* value changes from 0 corresponding to black to 100 corresponding to white. The positive direction of the x-axis corresponds to a red direction, the positive direction of the y-axis corresponds to a yellow direction, the negative direction of the x-axis corresponds to a green direction, the negative direction of the y-axis corresponds to a blue direction, and the position on the x-axis is designated by a* of which value changes from −60 to +60 and the position on the y-axis is designated by b* of which value changes from −60 to +60. The hue and chroma are represented by a* value and b* value, respectively.

A lower L* represents a darker color (greater intensity).

The difference in overall coloring between colored hair swatches is defined by (ΔE*) according to the following equation:

$$\Delta E^* = \sqrt{(L^* - L_o^*)^2 + (a^* - a_o^*)^2 + (b^* - b_o^*)^2}$$

In this equation, L*, a* and b* represent the values measured on colored (treated) hair swatches and $L_o^*$, $a_o^*$ and $b_o^*$ represent the values measured on uncolored (untreated) hair swatches or hair swatches treated with a different composition. This allow for quantification of differences in color (color uptake or color retention) between untreated versus treated hair swatches or between different samples of treated hair swatches. Typically, a ΔE* value (or simply ΔE) of 2 or greater between two samples is noticeable with the naked eye (human). The results are presented in the table below.

| Treatment | ΔE |
| --- | --- |
| 0.1 wt. % of Direct Dye in Inventive Composition | 9.47 |
| 0.25 wt. % of Direct Dye in Inventive Composition | 17.93 |
| 0.4 wt. % of Direct Dye in Inventive Composition | 28.48 |
| 0.5 wt. % of Direct Dye in Inventive Composition | 27.58 |
| 0.5 wt. % of Direct Dye in Water | 5.02 |
| 0.5 wt. % of Direct Dye in Organic Solvent | 2.33 |
| Treatment with Commercial Conditioner | 3.29 |

The data show that compositions of the instant disclosure provide a surprising degree of color deposition. Including the direct dye with water, organic solvent, or with an with a commercial conditioner did not provide any appreciable amount of color deposition. In fact, treatment with the direct dye in the organic solvent provided less color change than treatment with the commercial conditioner. Application of the direct dye in water provided a very slight change in color, but the change was not statistically significant.

Example 4

Effectiveness of Anionic Direct Dyes

Testing was carried out to determine how the technology of the instant disclosure contributes to coloring using direct dyes. The base composition of Composition A was used to test four different direct dyes: Ext. Violet 2 (Composition A), Green 5, Orange 4, and Red 40. Each direct dye was added into the base composition in an amount of 0.5 wt. %, based on the total weight of the final composition. Bleached hair swatches were treated with the four different coloring compositions. Hair swatches of 90% grey virgin hair, 90% grey permed hair, and level 7 bleached hair were treated. The color of the swatches was determined immediately after the coloring treatment. The swatches were then shampooed and the color of the swatches was again determined. The swatches were then shampooed a second time and the color of the swatches was again determined after the second shampooing. All compositions tested quickly and efficiently colored the hair.

Example 5

Improved Color Uptake of Anionic Direct Dyes Using Thickening Agent

Testing was carried out to determine the influence of a thickening agent (VP/VA copolymer) on color uptake. Composition A was used to test four different direct dyes: Ext. Violet 2 (Composition F), Green 5, Orange 4, and Red 40. Each direct dye was added into Composition A in an amount of 0.5 wt. %, based on the total weight of the final composition. Bleached hair swatches were treated with one of the four different coloring compositions. To determine whether the addition of VP/VA copolymer impacted color deposition, the same four coloring composition were prepared but 1 wt. % of VP/VA copolymer was added. This resulted in four different thickened coloring compositions. These thickened coloring compositions were used to treat bleach hair swatches. Hair swatches treated with the thickened coloring compositions were compared with the hair swatches treated unthickened coloring compositions. The results showed a statistically significant enhancement of color update for the thickened coloring compositions. In other words, it was surprisingly discovered that addition of VP/VA copolymer improved (to a statistically significant degree) the color update of anionic direct dyes.

Example 6

Additional Thickening with Hydroxypropylcellulose

Testing was carried out to determine how additional thickening might influence color uptake. This was carried out by comparing the color uptake of Compositions A, D, and E. All compositions include the same type and amount of direct dye (Ext. Violet 2 at 0.5 wt. %). Composition A does not include any thickening agents. Composition D includes VP/VA copolymer. Composition F includes both VP/VA copolymer and hydroxypropylcellulose. VP/VA copolymer thickened the coloring composition and also enhanced color uptake (also shown above in Example 5). The addition of hydroxypropylcellulose further thickened the composition and did not negatively influence the improved color uptake provided by the VP/VA copolymer.

Example 7

Improved Color Uniformity with Cationic Direct Dyes

Testing was carried out to compare the substantially anhydrous compositions of the instant disclosure with aqueous compositions. Bleached hair swatches were treated with Compositions F, G, and H. For comparison, the same amount of direct dye included in Composition F (0.1 wt. % of Basic Red 51) and Composition G (0.04 wt. % of Basic Red 51) was added to water to create comparative, aqueous compositions. These comparative, aqueous compositions were used to treat bleached hair swatches in the same manner as the bleached hair swatches treated with Compositions F, G, and H. Expert comparison of the results found that hair treated with Compositions F, G, and H exhibit uniform color deposition. The hair swatches treated with the comparative, aqueous compositions were not uniformly colored but found to be "spotty" (non-uniform color deposition).

Example 8

Compositions with Oxidative Dye Precursors

Example 9

Color Deposition of Oxidative Dyes

Testing was carried out to determine the color deposition provided by the oxidative dye precursors in the coloring compositions of Example Formulas I-L. Two sets of hair swatches were treated with each of Example Formulas I-L. The first set of hair swatches was bleached one time to a Level 7 bleaching standard. The second set of hair swatches were 90% grey permed hair swatches.

Example Formulas I-L were mixed by hand with a developer containing an oxidizing agent and subsequently applied to the hair swatches. Specifically, about 0.5 grams of coloring composition was mixed with about 0.5 grams of the developer for 1 minute prior to being applied to the respective hair swatches. The hair coloring compositions of Example Formulas I-L were left on the respective hair swatches for about 20 minutes before thoroughly rinsing the hair swatches.

The hair swatches were evaluated using the CIE L*a*b* system using a Minolta Spectrophotometer CM3600D colorimeter. As discussed above, in the L*a*b* system, the three parameters simply denote, respectively, the color intensity (L*), the green/red color axis (a*) and the blue/yellow color axis (b*). The L*a*b* colorimetric system is a colorimetric system that assigns each color to a position in a spherical color space. The brightness is represented by a position in the ordinate (z-axis) direction, the hue is represented by a position in the circumferential direction, and the chroma is represented by a distance from the center axis. The position on the ordinate (z-axis) representing brightness is designated by L*, and the L* value changes from 0 corresponding to black to 100 corresponding to white. The positive direction of the x-axis corresponds to a red direction, the positive

| | INCI US | I (wt. %) | J (wt. %) | K (wt. %) | L (wt. %) |
|---|---|---|---|---|---|
| Oxidative Dye Precursors | m-AMINOPHENOL; 2,4-DIAMINOPHENOXYETHANOL HCL; TOLUENE-2,5-DIAMINE; p-PHENYLENEDIAMINE; p-AMINOPHENOL; 2-AMINO-3-HYDROXYPYRIDINE; 4-AMINO-2-HYDROXYTOLUENE; RESORCINOL; and N,N-BIS(2-HYDROXYETHYL)-p-PHENYLENEDIAMINE SULFATE | 0.4 | 0.4 | 0.95 | 0.95 |
| Mono-alcohol | ETHANOL | 10 | 10 | 10 | 10 |
| Glycol | PROPYLENE GLYCOL | 41.5 | 81.5 | 80.95 | 40.95 |
| | HEXYLENE GLYCOL | 40 | | | 40 |
| Ratio of glycol to mono-alcohol | | 8.15 | 8.15 | 8.1 | 8.1 |
| Cationic Surfactant | CETRIMONIUM CHLORIDE | 0.6 | 0.6 | 0.6 | 0.6 |
| Fatty Ester | DICAPRYLYL CARBONATE | 0.9 | 0.9 | 0.9 | 0.9 |
| Fatty Alcohol | MYRISTYL ALCOHOL | 2 | 2 | 2 | 2 |
| Thickening agent | VP/VA COPOLYMER | 1 | 1 | 1 | 1 |
| Reducing Agent | AMMONIUM THIOLACTATE; THIOGLYCERIN; and SODIUM METABISULFITE | ≤0.3 | ≤0.3 | ≤0.3 | ≤0.3 |
| Water | WATER | 1.97 | 1.97 | 1.97 | 1.97 |
| Antioxidant | ERYTHORBIC ACID and TOCOPHEROL | 0.4 | 0.4 | 0.4 | 0.4 |
| Fragrance | FRAGRANCE | 1 | 1 | 1 | 1 | direction of the y-axis corresponds to a yellow direction, the negative direction of the x-axis corresponds to a green direction, the negative direction of the y-axis corresponds to a blue direction, and the position on the x-axis is designated by a* of which value changes from −60 to +60 and the position on the y-axis is designated by b* of which value changes from −60 to +60. The hue and chroma are represented by a* value and b* value, respectively.

The difference in overall coloring between colored hair swatches is defined by (ΔE*) according to the following equation:

$$\Delta E^* = \sqrt{(L^* - L_o^*)^2 + (a^* - a_o^*)^2 + (b^* - b_o^*)^2}$$

In the above equation, $L^*$, $a^*$ and $b^*$ represent the values measured on colored (treated) hair swatches and $L_o^*$, $a_o^*$ and $b_o^*$ represent the values measured on uncolored (untreated) hair swatches or hair swatches treated with a different composition. This allows for the quantification of differences in color (color uptake or color retention) between untreated versus treated hair swatches or between different samples of treated hair swatches. Typically, a ΔE* value (or simply ΔE) of 2 or greater between two samples is noticeable with the naked eye (human). ΔL represents the change in the color intensity of the hair swatch after application of the coloring composition as compared to before application of the coloring composition. The results are presented in the table below.

|  |  | Hair Swatch (Level 7 bleached 1x) | Hair Swatch (90% grey permed hair) |
|---|---|---|---|
| Example Formula I | ΔL | −33.73 | −11.29 |
| Example Formula I | ΔE | 39.02 | 12.39 |
| Example Formula J | ΔL | −28.38 | −9.03 |
| Example Formula J | ΔE | 33.41 | 10.19 |
| Example Formula K | ΔL | −44.77 | −22.16 |
| Example Formula K | ΔE | 51.00 | 24.50 |
| Example Formula L | ΔL | −44.51 | −25.35 |
| Example Formula L | ΔE | 50.91 | 28.08 |

The data show that compositions of the instant disclosure provide a surprising degree of color deposition.

Example 10

Color Deposition of Oxidative Dyes

Testing was carried out to determine the color deposition provided by the oxidative dye precursors in the coloring compositions of Example Formulas I-L. Similar to Example 9, the hair coloring compositions of Example Formulas I-L were applied to a first set of hair swatches bleached one time to a Level 7 bleaching standard and a second set of hair swatches having 90% grey permed hair.

Prior to applying Example Formulas I-L, about 0.5 grams of developer was applied to each of the hair swatches. About 0.5 grams of the hair coloring compositions of Example Formulas I-L were then applied to the respective hair swatches for about 20 minutes before thoroughly rinsing the hair swatches.

The hair swatches were evaluated using the CIE L*a*b* system using a Minolta Spectrophotometer CM3600D colorimeter, as discussed in Examples 3 and 9. The results are presented in the table below.

|  |  | Hair Swatch (Level 7 bleached 1x) | Hair Swatch (90% grey permed hair) |
|---|---|---|---|
| Example Formula I | ΔL | −29.35 | −14.68 |
| Example Formula I | ΔE | 35.28 | 16.13 |
| Example Formula J | ΔL | −28.03 | −12.39 |
| Example Formula J | ΔE | 33.71 | 13.35 |
| Example Formula K | ΔL | −43.43 | −21.66 |
| Example Formula K | ΔE | 49.31 | 23.98 |
| Example Formula L | ΔL | −42.52 | −28.32 |
| Example Formula L | ΔE | 48.7 | 30.97 |

The data show that compositions of the instant disclosure provide a surprising degree of color deposition.

Example 11

Compositions with Oxidative Dye Precursors and Direct Dyes

|  | INCI US | M (wt. %) |
|---|---|---|
| Oxidative Dye Precursors | p-PHENYLENEDIAMINE; p-AMINOPHENOL; RESORCINOL; and m-AMINOPHENOL | 0.54 |
| Direct Dye | 3-NITRO-P-HYDROXYETHYLAMINOPHENOL; 2-AMINO-6-CHLORO-4-NITROPHENOL; and 2-NITRO-5-GLYCERYL METHYLANILINE | 0.43 |
| Mono-alcohol | ALCOHOL DENAT. | 10. |
| Glycol | PROPYLENE GLYCOL | 80.929 |
| Ratio of glycol to mono-alcohol | | 8.09 |
| Cationic Surfacant | CETRIMONIUM CHLORIDE | 0.6 |
| Fatty Ester | DICAPRYLYL CARBONATE | 0.89955 |
| Fatty Alcohol | MYRISTYL ALCOHOL | 2. |
| Thickener | VP/VA COPOLYMER | 1. |
| Reducing Agent | AMMONIUM THIOLACTATE | 0.232 |
|  | SODIUM METABISULFITE | 0.00054 |
| Water | WATER | 1.968 |
| Antioxidant | ERYTHORBIC ACID and TOCOPHEROL | 0.4 |
| Fragrance | FRAGRANCE | 1 |

Example 12

Color Deposition of Oxidative Dye Precursors and Direct Dyes

Testing was carried out to determine the color deposition provided by the oxidative dye precursors and direct dyes in the coloring composition of Example Formula M. Two types of swatches were treated with Example Formula M—namely a first hair swatch that was bleached one time to a Level 7 bleaching standard and a second hair swatch with 90% grey permed hair swatches.

Example Formula M was mixed by hand with a developer and subsequently applied to the hair swatches. Specifically, about 0.5 grams of the coloring composition of Example Formula M was mixed with about 0.5 grams of the developer for 1 minute prior to being applied to the respective hair swatches. The hair coloring composition of Example Formula M was left on the respective hair swatches for about 20 minutes before thoroughly rinsing the hair swatches.

The hair swatches were evaluated using the CIE L*a*b* system using a Minolta Spectrophotometer CM3600D colorimeter, as discussed in Examples 3 and 9. The results are presented in the table below.

|  |  | Hair Swatch (Level 7 bleached 1x) | Hair Swatch (90% grey permed hair) |
|---|---|---|---|
| Example Formula M | ΔL ΔE | −49.04 52.89 | −20.87 25.64 |

The data show that compositions of the instant disclosure provide a surprising degree of color deposition.

Example 13

Color Deposition of Oxidative Dye Precursors and Direct Dyes

Testing was carried out to determine the color deposition provided by the oxidative dye precursors and direct dyes in the coloring composition of Example Formula M. Similar to Example 12, the hair coloring compositions of Example Formula M was applied to a first hair swatch bleached one time to a Level 7 bleaching standard and a second hair swatch having 90% grey permed hair.

Prior to applying Example Formula M, about 0.5 grams of developer was applied to each hair swatch. About 0.5 grams of the hair coloring compositions of Example Formula M was then applied to the respective hair swatches for about 20 minutes before thoroughly rinsing the hair swatches.

The hair swatches were evaluated using the CIE L*a*b* system using a Minolta Spectrophotometer CM3600D colorimeter, as discussed in Examples 3 and 9. The results are presented in the table below.

|  |  | Hair Swatch (Level 7 bleached 1x) | Hair Swatch (90% grey permed hair) |
|---|---|---|---|
| Example Formula M | ΔL ΔE | −50.30 53.95 | −21.63 26.49 |

The data show that compositions of the instant disclosure provide a surprising degree of color deposition.

Example 14

Compositions with Direct Dyes

|  | INCI US | N (wt. %) | O (wt. %) | P (wt. %) |
|---|---|---|---|---|
| Direct Dye | EXT. VIOLET 2 | 0.1 | 0.1 | 0.1 |
| Propylene Glycol | PROPYLENE GLYCOL | 82 | 84 | 84 |
| Mono-Alcohol | Ethanol | 10 | 10 | 10 |
| Ratio of Propylene Glycol to Mono-Alcohol |  | 8.2 | 8.4 | 8.4 |
| Cationic Surfactant | CETRIMONIUM CHLORIDE | 0.65 |  |  |
|  | STEARAMIDOPROPYL DIMETHYLAMINE |  | 0.75 | 0.75 |
| Fatty Ester | DICAPRYLYL CARBONATE | 0.9 | 0.9 | 0.9 |
| Fatty Alcohol | MYRISTYL ALCOHOL | 2 | 2 | 2 |
| Fatty Acid | PALMITIC ACID |  |  | 0.52 |
| Thickening Agent | VP/VA COPOLYMER | 1 | 1 | 1 |
| Misc. | Fragrance and Preservatives | ~1 | ~1 | ~1 |
| Water | WATER | 1.95 |  |  |

Example 14

Color Deposition of Direct Dyes

Testing was carried out to determine the color deposition provided by the coloring compositions of Formulas N-P. Formulas N-P were applied to two sets of hair swatches. The first set of hair swatches was bleached one time to a Level 7 bleaching standard. The second set of hair swatches were 90% grey permed hair swatches. Both sets of hair swatches were wet with water and then squeezed by hand to remove excess water.

2.5 grams of Formulas N-P were applied per gram of hair to the respective hair swatches. A stylist color brush was used to ensure a uniform application of the hair coloring compositions. After about 5 minutes, the hair swatches were rinsed under warm water using a moderate water flow while being squeezed 8 times by passing ones fingers over the hair. The hair swatches were subsequently squeezed by passing ones fingers over the hair of the hair swatches 2 additional times. A blow dryer was then used to dry the hair swatches.

The hair swatches were evaluated using the CIE L*a*b* system using a Minolta Spectrophotometer CM3600D colorimeter, as discussed in Examples 3 and 9. The results are presented in the table below.

|  |  | Hair Swatch (Level 7 bleached 1x) | Hair Swatch (90% grey permed hair) |
|---|---|---|---|
| Example Formula N | ΔL ΔE | −13.8 25.4 | −12.62 21.75 |
| Example Formula O | ΔL ΔE | −3.22 7.79 | −11.25 18.59 |
| Example Formula P | ΔL ΔE | −1.66 5.75 | −9.89 14.57 |

The hair coloring composition of Formula N exhibited significantly higher direct dye deposit than the compositions of Formula 0 and P on both the Level 7 bleached hair swatch and 90% grey permed hair swatch. While not being limited to any particular theory, the inventors believe that the use of a composition such as Formula N, that contained a combination of a cationic surfactant chosen from a quaternary ammonium salt (e.g., cetrimonium chloride) and a fatty alcohol (e.g. myristyl alcohol) resulted in improved/enhanced color deposition. It is also believed that the combination of a cationic surfactant chosen from a quaternary ammonium salt (e.g., cetrimonium chloride) and a fatty alcohol (e.g. myristyl alcohol) resulted in a lamellar formation in Formula N in the presence of water that provided improved/enhanced color deposition.

The terms "comprising," "having," and "including" are used in their open, non-limiting sense.

The terms "a" and "the" are understood to encompass the plural as well as the singular.

The compositions (e.g., the "nanoemulsions") and methods of the present disclosure can comprise, consist of, or consist essentially of the essential elements and limitations of the disclosure described herein, as well as any additional or optional ingredients, components, or limitations described herein or otherwise useful.

All percentages, parts and ratios herein are based upon the total weight of the compositions of the present disclosure, unless otherwise indicated.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

Other than in the operating examples, or where otherwise indicated, all numbers expressing quantities of ingredients and/or reaction conditions are to be understood as being modified in all instances by the term "about," meaning within +/−5% of the indicated number.

As used herein, the expression "at least one" is interchangeable with the expression "one or more" and thus includes individual components as well as mixtures/combinations.

The term "substantially free" or "essentially free" as used herein means that there is less than about 5% by weight of a specific material added to a composition, based on the total weight of the compositions. Nonetheless, the compositions may include less than about 2 wt. %, less than about 1 wt. %, less than about 0.5 wt. %, less than about 0.1 wt. %, less than 0.01 wt. %, or none of the specified material.

The term "active material" as used herein with respect to the percent amount of an ingredient or raw material, refers to 100% activity of the ingredient or raw material.

"Cosmetically acceptable" means that the item in question is compatible with a keratinous substrate such as skin and hair. For example, a "cosmetically acceptable carrier" means a carrier that is compatible with a keratinous substrate such as skin and hair. The nanoemulsions described herein are preferably cosmetically acceptable.

Throughout the disclosure, the term "a mixture thereof" may be used following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be included, or a mixture of any two of A, B, C, D, E, F, a salt of A, a salt of B, a salt of C, a salt of D, a salt of E, and a salt of F may be included.

The salts referred to throughout the disclosure may include salts having a counter-ion such as an alkali metal, alkaline earth metal, or ammonium counter-ion. This list of counter-ions, however, is non-limiting.

The expression "inclusive" for a range of concentrations means that the limits of the range are included in the defined interval.

"Volatile", as used herein, means having a flash point of less than about 100° C.

"Non-volatile", as used herein, means having a flash point of greater than about 100° C.

The term "polymers," as defined herein, include homopolymers and copolymers formed from at least two different types of monomers.

The term "INCI" is an abbreviation of International Nomenclature of Cosmetic Ingredients, which is a system of names provided by the International Nomenclature Committee of the Personal Care Products Council to describe personal care ingredients.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

All components and elements positively set forth in this disclosure can be negatively excluded from the claims. In other words, the compositions (nanoemulsions) of the instant disclosure can be free or essentially free of all components and elements positively recited throughout the instant disclosure.

Some of the various categories of components identified may overlap. In such cases where overlap may exist and the composition includes both components (or the composition includes more than two components that overlap), an overlapping compound does not represent more than one component. For example, a fatty acid may be characterized as both a nonionic surfactant and a fatty compound. If a particular composition includes both a nonionic surfactant and a fatty compound, a single fatty acid will serve as only the nonionic surfactant or as only the fatty compound (the single fatty acid does not serve as both the nonionic surfactant and the fatty compound).

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A coloring composition that is substantially anhydrous comprising:
    (a) one or more colorants comprising at least one of an oxidative dye precursor, a coupler, a direct dye, or a combination thereof;
    (b) about 50 to about 90 wt. % of one or more glycols;
    (c) about 5 to about 30 wt. % of one or more monoalcohols chosen from ethanol, isopropyl alcohol, and a mixture thereof;
        wherein the weight ratio of the glycol(s) to the monoalcohol(s) (glycol(s): monoalcohol(s)) is from 20:1 to 2:1;
    (d) about 0.1 to about 10 wt. % of one or more cationic surfactants;
    (e) about 1 to about 20 wt. % of one or more fatty compounds;
        wherein the composition comprises less than 5 wt. % of water;
        the composition is a solubilized, non-emulsified composition until applied to the wet or damp hair, whereupon the composition forms a lamellar phase in situ; and
        all percentages by weight are based on the total weight of the composition.

2. A coloring composition that is substantially anhydrous comprising:
    (a) one or more colorants comprising at least one of an oxidative dye precursor, a coupler, a direct dye, or a combination thereof, wherein when the one or more colorant comprises a direct dye, the direct dye is selected from nitro-phenylenediamines, nitro-aminophenols, azo dyes, anthraquinones, triarylmethane dyes, indophenols, and a combination thereof, and wherein when the one or more colorant comprises an oxidative dye precursor, the oxidative dye precursor is selected from ortho aminophenols, para aminophenols, ortho phenylenediamines, para phenylenediamines, double bases, heterocyclic bases, m-aminophenol, 2,4-diaminophenoxyethanol hcl, toluene-2,5-diamine thioglycerin, p-aminophenol, 2-amino-3 hydroxypyridine, 4-amino-2-hydroxytoluene, acid addition salts thereof, and a combination thereof;

(b) about 50 to about 90 wt. % of one or more glycols selected from ethylene glycol, propylene glycol, butylene glycol, hexylene glycol, pentylene glycol, 1,3-propanediol, diethylene glycol, dipropylene glycol, caprylyl glycol, glycerin, and a mixture thereof;

(c) about 5 to about 30 wt. % of ethanol;

wherein the weight ratio of the glycol(s) to ethanol (glycol: ethanol) is from 18:1 to 2:1;

(d) about 0.1 to about 10 wt. % one or more cationic surfactants;

(e)(i) about 0.1 to about 10 wt. % of one or more fatty esters selected from fatty carbonate esters, glycerol fatty esters, sucrose fatty esters, sorbitan fatty ester, fatty acid esters, or mixtures thereof;

(e)(ii) about 0.1 to about 10 wt. % of one or more fatty alcohols selected from cetearyl alcohol, stearyl alcohol, behenyl alcohol, cetyl alcohol, myristyl alcohol, isostearyl alcohol, lauryl alcohol, and a mixture thereof;

wherein the composition is a solubilized, non-emulsified composition until applied to wet or damp hair, whereupon the composition forms a lamellar phase in situ;

the composition comprises less than 5 wt. % of water; and all percentages by weight are based on the total weight of the composition.

3. The composition of claim 2 comprising:

(a) one or more colorants comprising at least one of an oxidative dye precursor, a coupler, a direct dye, or a combination thereof, wherein when the one or more colorant comprises a direct dye, the direct dye is selected from nitro-phenylenediamines, nitro-aminophenols, azo dyes, anthraquinones, triarylmethane dyes, indophenols, and a combination thereof, and wherein when the one or more colorant comprises an oxidative dye precursor, the oxidative dye precursor is selected from ortho aminophenols, para aminophenols, ortho phenylenediamines, para phenylenediamines, double bases, heterocyclic bases, m-aminophenol, 2.4-diaminophenoxyethanol hcl, toluene-2,5-diamine thioglycerin, p-aminophenol, 2-amino-3 hydroxypyridine, 4-amino-2-hydroxytoluene, acid addition salts thereof, and a combination thereof;

(b) about 50 to about 90 wt. % of propylene glycol, hexylene glycol, or a mixture thereof;

(c) about 5 to about 30 wt. % of ethanol;

(d) about 0.1 to about 10 wt. % of one or more cationic surfactants selected from cetrimonium chloride, behentrimonium chloride, behentrimonium methosulfate, stearamidopropyl dimethylamine, and a mixture thereof;

(e)(i) about 0.1 to about 10 wt. % of one or more fatty carbonate esters selected from dialkyl carbonates of formula: $R_1O(C=O)R_2$, wherein $R_1$ and $R_2$ are independently linear or branched, saturated or unsaturated alkyl chains having 6 to 22 carbon atoms; and (e)(ii) about 0.1 to about 10 wt. % of one or more fatty alcohols selected from cetearyl alcohol, stearyl alcohol, behenyl alcohol, cetyl alcohol, myristyl alcohol, isostearyl alcohol, and a mixture thereof.

* * * * *